(12) United States Patent
Mayne et al.

(10) Patent No.: US 7,928,189 B2
(45) Date of Patent: Apr. 19, 2011

(54) PCSK9 POLYPEPTIDE FRAGMENT

(75) Inventors: Janice Mayne, Ottawa (CA); Michel Chrétien, Ottawa (CA); Majambu Mbikay, Ottawa (CA)

(73) Assignee: Ottawa Health Research Institute, Ottawa (CA)

( * ) Notice: Subject to any disclaimer, the term of this patent is extended or adjusted under 35 U.S.C. 154(b) by 0 days.

(21) Appl. No.: 12/115,382

(22) Filed: May 5, 2008

(65) Prior Publication Data

US 2009/0275504 A1 Nov. 5, 2009

(51) Int. Cl.
*A61K 38/10* (2006.01)
*C07H 21/04* (2006.01)
*C12N 15/11* (2006.01)

(52) U.S. Cl. ........ 530/326; 536/23.2; 536/23.5; 514/14; 435/320.1

(58) Field of Classification Search .................... None
See application file for complete search history.

(56) References Cited

U.S. PATENT DOCUMENTS

| | | | |
|---|---|---|---|
| 3,538,214 A | 11/1970 | Polli et al. | |
| 4,601,894 A | 7/1986 | Hanna et al. | |
| 4,680,323 A | 7/1987 | Lowey | |
| 4,687,757 A | 8/1987 | Parrott et al. | |
| 4,994,276 A | 2/1991 | Baichwal et al. | |
| 5,504,190 A * | 4/1996 | Houghten et al. | 530/329 |
| 5,679,647 A | 10/1997 | Carson et al. | |
| 5,739,118 A | 4/1998 | Carrano et al. | |
| 5,837,533 A | 11/1998 | Boutin | |

FOREIGN PATENT DOCUMENTS

| | | |
|---|---|---|
| WO | WO 92/06180 | 4/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 93/25234 | 12/1993 |
| WO | WO 94/06920 | 3/1994 |
| WO | WO 02/45695 | 6/2002 |

OTHER PUBLICATIONS

Dewpura et al, 2008. FEBS Journal. 275: 3480-3493.*
Seidah et al, 2003. PNAS. 100(3): 928-933.*
Record for GenBank Accession No. NP_777596 (May 17, 2009, 4 pages as printed).*
Record for GenBank accession No. AX127530 (Apr. 16, 2005; 3 pages as printed).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Phillips, A., J Pharm Pharmacology 53: 1169-1174, 2001.*
Altschul et al., "Basic Local Alignment Search Tool," *J. Mol. Biol* 215: 403-410 (1990).

(Continued)

*Primary Examiner* — Bridget E Bunner
*Assistant Examiner* — Zachary C Howard
(74) *Attorney, Agent, or Firm* — Clark & Elbing LLP

(57) ABSTRACT

The present invention provide PCSK9 polypeptides, fragments thereof and methods of modulating PCSK9 phosphorylation and low density lipoprotein degradation.

7 Claims, 14 Drawing Sheets

Representative Fragments of PCSK9

1. PCSK9(42-56)--NT      VLALRSEEDGLAEAP (SEQ ID NO:2)

2. PCSK9(42-56)Sp-NTP    VLALR[pS]EEDGLAEAP (SEQ ID NO:3)

3. PCSK9(CT)--CT         RSRHLAQASQELQ (SEQ ID NO:4)

4. PCSK9(CT)[pS]--CTP    RSRHLAQA[pS]QELQ (SEQ ID NO:5)

where pS refers to phosphoserine

OTHER PUBLICATIONS

Berkner et al., "Development of Adenovirus Vectors for the Expression of Heterologous Genes," *BioTechniques* 6: 616-629 (1988).

Cornejo et al., "Activity of a Maize Ubiquitin Promoter in Transgenic Rice," *Plant. Mol. Biol.* 23: 567-581 (1993).

Etienne-Julan et al., "The Efficiency of Cell Targeting by Recombinant Retroviruses Depends on the Nature of the Receptor and the Composition of the Artificial Cell-Virus Linker," *Journal of General Virology* 73: 3251-3255 (1992).

Feigner and Rhodes, "Gene Therapeutics," *Nature* 349: 351-352 (1991).

Goud et al., "Antibody-Mediated Binding of a Murine Ecotropic Moloney Retroviral Vector to Human Cells Allows Internalization But Not the Establishment of the Proviral State," *Virology* 163: 251-254 (1988).

Graham et al., "Manipulation of Adenovirus Vector," *Methods in Molecular Biology* 7: 109-128 (1991).

Haj-Ahmand and Graham., "Development of a Helper-Independent Human Adenovirus Vector and Its Use in the Transfer of the Herpes Simplex Virus Thymidine Kinase Gene," *J. Virol.* 163:267-274 (1986).

Holtorf et al., "Comparison of Different Constitutive and Inducible Promoters for the Overexpression of Transgenes in *Arabidopsis thaliana*," *Plant Mol. Biol.* 29: 637-646 (1995).

Jones et al., "Evolution of Two Major Chorion Multigene Families as Inferred from Cloned cDNA and Protein Sequences," *Cell* 18: 1317-1332 (1979).

Koller and Smithies, "Inactivating the $\beta_2$-Microglobulin Locus in Mouse Embryonic Stem Cells by Homologous Recombination," *Proc. Natl. Acad. Sci* USA 86: 8932-8935 (1989).

Mandel et al., "Definition of Constitutive Gene Expression in Plants: The Translation Initiation Factor 4A Gene as a Model," *Plant Molecular Biology* 29: 995-1004 (1995).

Miller, "Retrovirus Packaging Cells," *Human Gene Therapy* 1: 5-14 (1990).

Miller, A.D., "Progress Toward Human Gene Therapy," *Blood* 76: 271-278 (1990).

Neda et al., "Chemical Modification of an Ecotropic Murine Leukemia Virus Results in Redirection of Its Target Cell Specificity," *J. Biol Chem* 266: 14143-14146 (1991).

Odell et al., "Identification of DNA Sequences Required for Activity of the Cauliflower Mosaic Virus 35S Promoter," *Nature* 313:810-812 (1985).

Rosenfeld et al., "In Vivo Transfer of the Human Cystic Fibrosis Transmembrane Conductance Regulator Gene to the Airway Epithelium," *Cell* 68:143-155 (1992).

Rosenfeld, "Adenovirus-Mediated Transfer of a Recombinant $\alpha$1-Antitrypsin Gene to the Lung Epithelium in Vivo," *Science* 252:431-434 (1991).

Roux et al., "A Versatile and Potentially General Approach to the Targeting of Specific Cell Types by Retroviruses: Application to the Infection of Human Cells by Means of Major Histocompatibility Complex Class I and Class II Antigens by Mouse Ecotropic Murine Leukemia Virus-Derived Viruses," *Proc. Natl. Acad. Sci.* USA 86:9079-9083 (1989).

Tatusova et al., "BLAST 2 Sequences, A New Tool for Comparing Protein and Nucleotide Sequences," *FEMS Microbiology Letters* 174: 247-250 (1999).

Wu and Wu, "Receptor-Mediated in Vitro Gene Transformation by a Soluble DNA Carrier System," *J. Biol. Chem.* 262: 4429-4432 (1987).

Xu et al., "Rice Triosephosphate Isomerase Gene 5' Sequence Directs $\beta$-Glucuronidase Activity in Transgenic Tobacco but Requires an Intron for Expression in Rice," *Plant Physiol.* 106: 459-467 (1994).

Zhang et al., "Analysis of Rice *Act1* 5' Region Activity in Transgenic Rice Plants," *Plant Cell* 3:1155-1165 (1991).

Zijlstra et al., "Germ-Line Transmission of a Disrupted $\beta_2$-Microglobulin Gene Produced by Homologous Recombination in Embryonic Stem Cells," *Nature* 342: 435-438 (1989).

* cited by examiner

Figure 1A. PCSK9 (*Homo sapiens*)

```
1    mgtvssrrsw wplplllll lllgpagara qededgdyee lvlalrseed glaeapehgt
61   tatfhrcakd pwrlpgtyvv vlkeethlsq sertarrlqa qaarrgyltk ilhvfhgllp
121  gflvkmsgdl lelalklphv dyieedssvf aqsipwnler itppryrade yqppdggslv
181  evylldtsiq sdhreiegrv mvtdfenvpe edgtrfhrqa skcdshgthl agvvsgrdag
241  vakgasmrsl rvlncqgkgt vsgtliglef irksqlvqpv gplvvllpla ggysrvlnaa
301  cqrlaragvv lvtaagnfrd daclyspasa pevitvgatn aqdqpvtlgt lgtnfgrcvd
361  lfapgediig assdcstcfv sqsgtsqaaa hvagiaamml saepeltlae lrqrlihfsa
421  kdvineawfp edqrvltpnl vaalppsthg agwqlfcrtv wsahsgptrm ataiarcapd
481  eellscssfs rsgkrrgerm eaqggklvcr ahnafggegv yaiarccllp qancsvhtap
541  paeasmgtrv hchqqghvlt gcsshweved lgthkppvlr prgqpnqcvg hreasihasc
601  chapgleckv kehgipapqe qvtvaceegw tltgcsalpg tshvlgayav dntcvvrsrd
661  vsttgstsee avtavaiccr srhlaqasqe lq
```

SEQ ID NO:1

Figure 1B. Representative Fragments of PCSK9

1. PCSK9(42-56)--NT      VLALRSEEDGLAEAP (SEQ ID NO:2)

2. PCSK9(42-56)Sp-NTP    VLALR[pS]EEDGLAEAP (SEQ ID NO:3)

3. PCSK9(CT)--CT         RSRHLAQASQELQ (SEQ ID NO:4)

4. PCSK9(CT)[pS]--CTP     RSRHLAQA[pS]QELQ (SEQ ID NO:5)

where pS refers to phosphoserine

Figure 5.
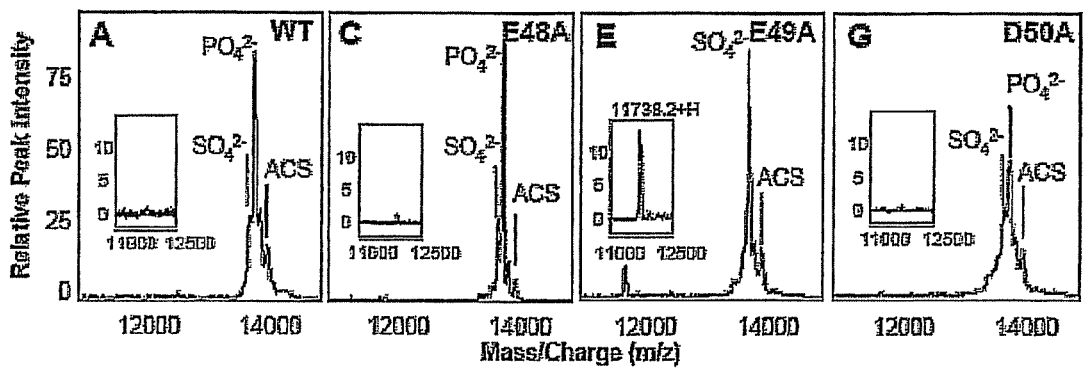
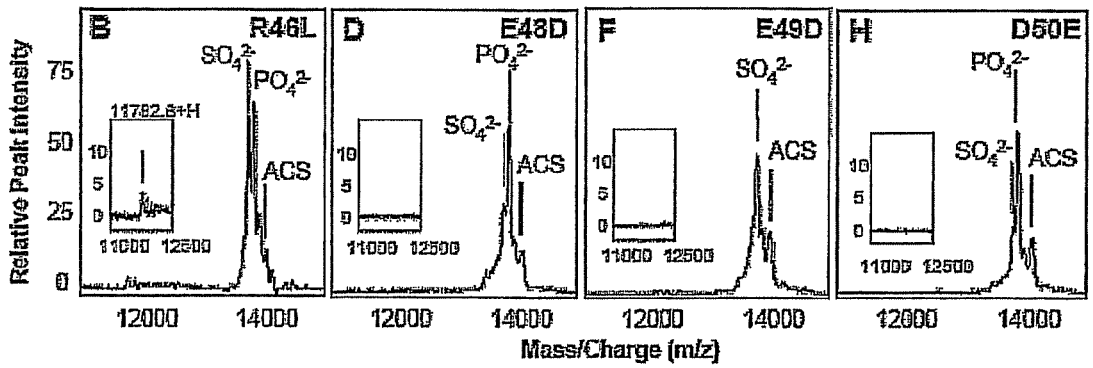

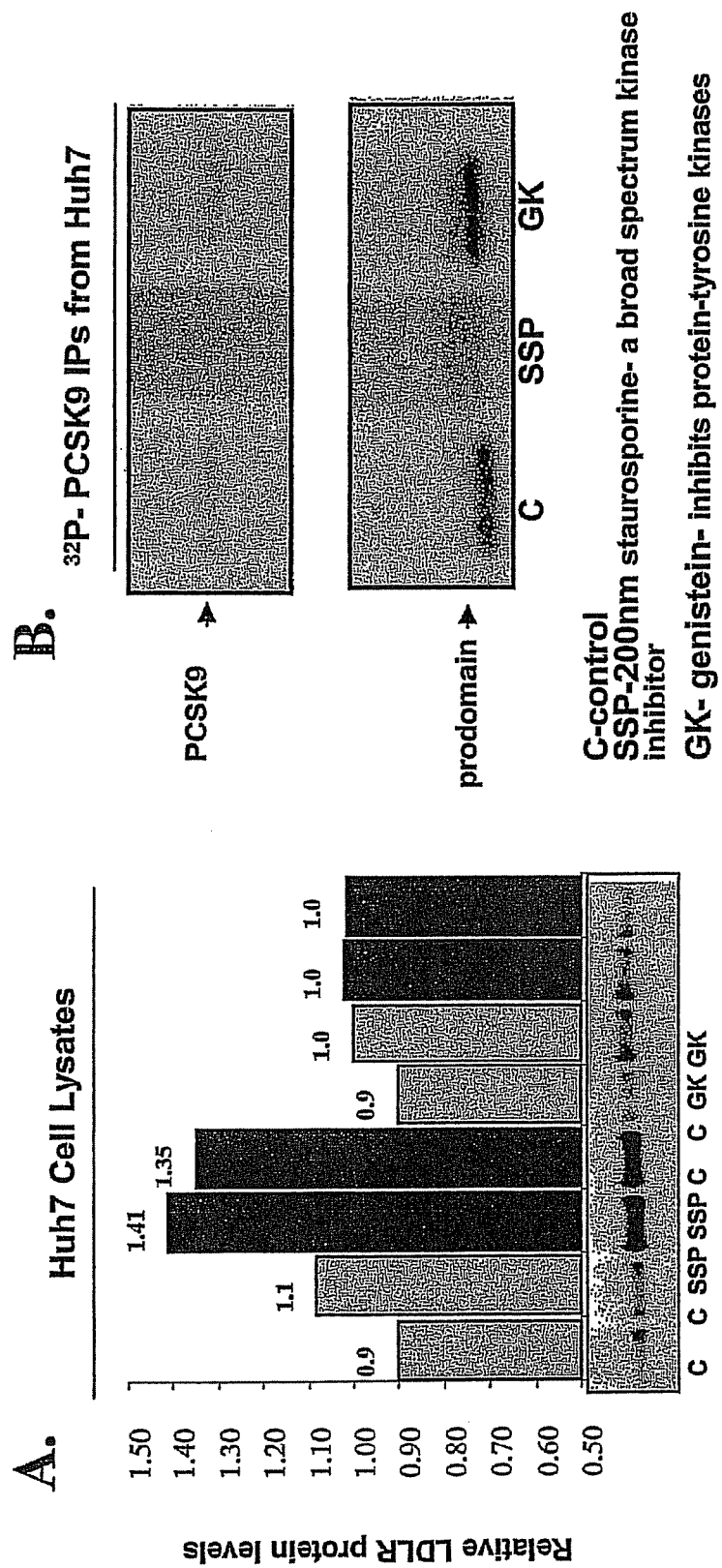
Figure 11A,B

PCSK9 POLYPEPTIDE FRAGMENT

FIELD OF THE INVENTION

The present invention relates to PCSK9 proteins, fragments thereof and methods of modulating PCSK9 phosphorylation and LDLR degradation.

BACKGROUND OF THE INVENTION

Proprotein convertase subtilisn/kexin 9 (PCSK9) is a member of the mammalian PCSK family that, to date, includes eight other members; PCSK1 (PC1/3), PCSK2 (PC2), PCSK (Furin), PCSK4 (PC4), PCSK5 (PC5/6), PCSK6 (Pace4), PCSK7 (PC7) and PCSK8 (SKI-1/S1P) [1]. Collectively this family is responsible for the proteolytic maturation of secretory precursors to bioactive proteins and peptides including neuropeptides, pro-hormones, cytokines, growth factors, receptors, cell surface proteins and serum proteins [2, 3]. Fitting with its role in cholesterol metabolism PCSK9 is highly expressed in the liver and intestine, two tissues important in cholesterol homeostasis [4]. It is also found in circulation [5-7]. PCSK9, like its family members, is synthesized as a preprotein containing several defined motifs; a signal peptide domain for routing the PCSKs to the secretory pathway, a prodomain important for folding and acting as an endogenous inhibitor, a catalytic domain characteristic of serine proteases, and a C-terminal Cys and His rich domain (CHRD) implicated in enzyme stability and protein-protein interaction [3]. We reported that PCSK9 is autocatalytically processed in the endoplasmic reticulum (ER) at the site FAQ152↓SIP indicative of its consensus cleavage motif, travels to the Golgi where its sugar residues at the glycosylation site N533CS are matured and its propeptide is sulfated at Tyr38, and is secreted [4,5]. PCSK9 is unique among the PCSK family because it is secreted in association with its inhibitory propeptide.

Cell culture and animal models have established that the low density lipoprotein receptor (LDLR) is one of the main down-stream targets of PCSK9 [4, 8-11]. Supporting this, several groups have reported that secreted PCSK9 can interact with and enter the endocytic recycling pathway with LDLR, affecting the equilibrium of LDLR recycling versus LDLR lysosomal-dependent degradation [6, 12-15]. The 'gain of function' D374Y variation in the catalytic domain of PCSK9 results in the most severe form of autosomal dominant hypercholesterolemia (ADH) [16,17]. Studies have shown that this variant binds the LDLR receptor (within its epidermal growth factor (EGF)-A domain) at the cell surface 25× more efficiently than wild type PCSK9 thereby shifting the equilibrium toward LDLR lysosomal-dependent degradation [12,15]. However the effect of other ADH-associated PCSK9 variants, such as the PCSK9(S127R) on PCSK9-LDLR dependent degradation is less obvious since their binding equilibrium to the LDLR is only moderately increased [15,18]. Crystal structures have shown that this Ser127 residue does not interact directly with the LDLR [19].

Longitudinal population studies have shown significant reduction in the risk of coronary heart disease (CHD) in 'loss of function' PCSK9 carriers [20,21]. Reduced plasma PCSK9 concentrations for at least three PCSK9 variants, R46L, Y142X and C679X increase the amount of LDLR that is recycled, effectively reducing plasma LDL cholesterol (LDLC) [7,22]. As is the case with 'gain of function' PCSK9 variants not all 'loss of function' variants can be attributed to a single mechanism, in this case, reduced plasma PCSK9. However these studies, along with the identification of two healthy PCSK9 'null' individuals [7,23] have generated much interest toward understanding the exact details of the mechanism(s) of PCSK9-dependent:LDLR degradation, its site(s) of action, whether the effect is direct or indirect, and how different PCSK9 SNPs alter its function. It is believed that the design of PCSK9 inhibitors may provide a promising therapy for treatment of hypercholesterolemia [7, 11, 24].

There is a need in the art for novel compounds that alter the interaction of PCSK9 with LDLR. There is also a need in the art for compounds that either inhibit or enhance LDLR degradation. Further, there is a need in the art for novel compounds that increase the amount of recycled LDLR thereby decreasing plasma low density lipoprotein C (LDLC). There is also a need in the art for novel compounds that alter the normal biological function of PCSK9. Further, there is a need in the art to understand and manipulate the mechanisms by which PCSK9 interacts with specific proteins including LDLR. There is also a need in the art to identify novel compounds and compositions that can modulate normal PCSK9 phosphorylation. Further, there is a need in the art for novel methods that may be employed to modulate PCSK9 phosphorylation.

SUMMARY OF THE INVENTION

The present invention relates to PCSK9 proteins, fragments thereof and methods of modulating PCSK9 phosphorylation and LDLR degradation.

According to the present invention, there is provided a PCSK9 polypeptide fragment comprising
  a) at least 7 consecutive amino acids of SEQ ID NO:1 or;
  b) an amino acid sequence that is at least 70% identical to the fragment defined in a).

The present invention also provides a PCSK9 polypeptide fragment as described above wherein the fragment comprises Serine 47, Serine 688, or both as defined by SEQ ID NO:1.

The present invention also provides the PCSK9 polypeptide fragment as defined above, wherein either Serine 47, 688 or both are phosphorylated.

The present invention also provides a PCSK9 polypeptide comprising the amino acid sequence as defined by SEQ ID NO:1, wherein the polypeptide is phosphorylated at Serine 47, Serine 688 or both.

The present invention also provides a PCSK9 polypeptide comprising one or more mutations, additions, deletions or a combination thereof in the amino acid sequence of SEQ ID NO:1.

The present invention also provides a nucleotide sequence encoding the PCSK9 polypeptide fragment as defined above and herein.

The present invention also provides a nucleotide sequence encoding the PCSK9 polypeptide as defined above and herein The present invention also provides a composition comprising the PCSK9 polypeptide or fragment thereof as defined above and a pharmaceutically acceptable carrier, diluent or excipient.

The present invention also provides a kit comprising,
  a) a PCSK9 polypeptide fragment thereof as defined above,
  b) the nucleic acid encoding the PCSK9 polypeptide fragment as defined above;
  c) the PCSK9 polypeptide as defined above;
  d) the nucleic acid encoding the PCSK polypeptide as defined above;
  e) one or more pharmaceutically acceptable carriers, diluents, or excipients;

f) one or more devices for delivering or administering one or more nucleic acids, PCSK polypeptides, fragments thereof or any combination thereof;

g) instructions for administering one or more nucleic acids, PCSK polypeptides, fragments thereof or any combination thereof or h) any combination or sub-combination of above.

The present invention also provides a nucleotide sequence as defined above, wherein the nucleotide sequence comprises a vector capable of expressing PCSK9 polypeptide fragment in vivo.

The present invention also provides a nucleotide sequence as defined above, wherein the nucleotide sequence comprises a vector capable of expressing PCSK9 polypeptide in vivo.

The present invention also provides the PCSK9 polypeptide fragment defined above, wherein the polypeptide fragment is defined by: VLALRSEEDGLAEAP (SEQ ID NO:2); VLALRS(phos)EEDGLAEAP (SEQ ID NO:3); RSRHLAQASQELQ (SEQ ID NO:4) or RSRHLAQAS(phos)QELQ (SEQ ID NO:5) wherein (phos) indicates phosphorylation of the preceding amino acid. Further, the polypeptides and fragments as defined herein are meant to include amino acids in the L-configuration, D-configuration or a combination of both.

The present invention also contemplates a method of modulating LDLR degradation comprising administering a compound that modulates LDLR degradation in a cell, cell culture or subject.

Also provided is a method as defined above wherein the compound is a PCSK9 polypeptide or polypeptide fragment.

Also provided is a method as defined above the modulating comprises protecting LDLR from degradation.

Also provided is a method as defined above wherein the protecting LDLR from degradation comprises administering an unphosphorylated PCSK9 polypeptide or polypeptide fragment of SEQ ID NO:1 that comprises Serine 47, a phosphorylated PCSK9 polypeptide or polypeptide fragment that comprises a phosphorylated or unphosphorylated Serine 688 to the cell, cell culture or subject to protect LDLR degradation.

Also provided is a method as defined above wherein the modulating comprises accentuating LDLR degradation comprising administering a phosphorylated PCSK9 polypeptide or polypeptide fragment of SEQ ID NO:1 that comprises phosphoSerine 47.

The present invention also provides a method as defined above, wherein the modulating comprises increasing LDLR levels and the method comprises administering a serine kinase inhibitor to the cell, cell culture or subject to increase LDLR levels.

The present invention also provides a method as defined above wherein the serine kinase inhibitor is a broad spectrum serine kinase inhibitor.

The present invention also provides an antibody against a PCSK9 polypeptide or a fragment thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A-B shows (A) the amino acid sequence of human PCSK9 proprotein (SEQ ID NO:1) and (B) representative fragments of PCSK9, where pS refers to phosphoserine.

FIG. 5A-H shows mass spectral analysis of the consensus site of PCSK9 propeptide phosphorylation from the media of transfected Huh7 cells overexpressing V5-tagged PCSK9 variants. A-H represent TOF-MS analyses of the propeptide of V5-tagged PCSK9 variants as labeled from the media of transfected and overexpressing Huh7 cells. For each variant the observed versus calculated (in brackets) molecular mass is shown below each panel for the sulfated ($SO_4^{2-}$) and sulfated and phosphorylated ($PO_4^{2-}$) propeptide, as well as the major molecular form observed. Insets highlight the presence or absence of proteolysis fragments of the parent propeptide. Analyses were conducted on at least 3 independent experiments. ns; non-specific. ACS; alternate signal peptidase cleavage site.

FIG. 11A,B shows results indicating that inhibition of PCSK9 phosphorylation by a kinase inhibitor leads to an increase in LDLR levels.

DESCRIPTION OF PREFERRED EMBODIMENT

Figure 2:
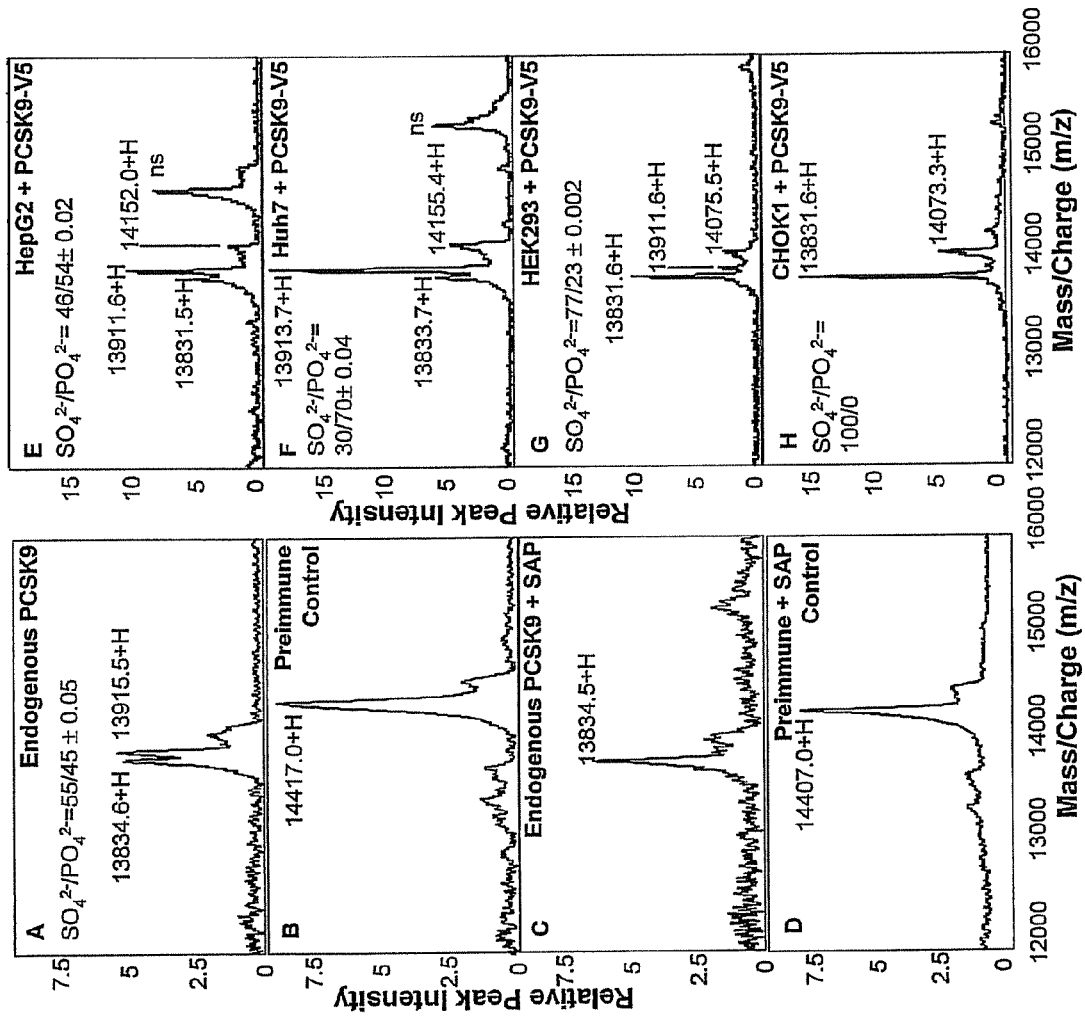
FIG. 2 (A-H) represent time-of-flight mass spectral analyses (TOF-MS) of the molecular forms of endogenously expressed PCSK9 propeptide immunoprecipitated from the media of HepG2 cells with either immune (anti-hPCSK9 Ab; A and C) or preimmune sera (B and D), and following dephosphorylation (C and D). E-H represent TOF-MS analyses of the molecular forms of the propeptide of V5-tagged PCSK9 immunoprecipitates from the media of transfected and overexpressing HepG2 (E), Huh7 (F), HEK293 (G) and CHOK1 (H) cells. The ratio of the sulfated ($SO_4^{2-}$) to sulfated and phosphorylated ($PO_4^{2-}$), calculated as area under the peak (AUP) as described in the Examples (see Materials and Methods), is shown plus or minus standard error. Analyses were conducted on at least 3 independent experiments. ns; non-specific.

The present invention relates to PCSK9 proteins, fragments thereof and methods of modulating PCSK9 phosphorylation.

The following description is of a preferred embodiment.

According to the present invention, there is provided a PCSK9 polypeptide or polypeptide fragment comprising,
  a) at least 7 consecutive amino acids of SEQ ID NO:1 or;
  b) an amino acid sequence that is at least 70% identical to the polypeptide or polypeptide fragment defined in a).
It is to be understood that the PCSK9 polypeptide fragment comprises part of the amino acid sequence of SEQ ID NO:1 but is not defined by SEQ ID NO:1. In addition, the present invention contemplates post-translationally modified PCSK9 polypeptides and polypeptide fragments as described and defined herein below.

Representative examples of PCSK9 polypeptide fragments contemplated by the present invention include, without limitation:
VLALRSEEDGLAEAP (SEQ ID NO:2); VLALR[pS]EEDGLAEAP (SEQ ID NO:3);
RSRHLAQASQELQ (SEQ ID NO:4); and RSRHLAQA[pS]QELQ (SEQ ID NO:5), where pS refers to phosphoserine.
Other PCSK9 polypeptides and fragments thereof for example, but not limited to mutants of SEQ ID NO:1 and fragments thereof as described herein and throughout are also contemplated by the present invention, but are not meant to be limiting in any manner.

A PCSK9 polypeptide or polypeptide fragment as defined herein comprises at least about 7 consecutive amino acids of SEQ ID NO:1 or an amino acid sequence that is at least 70% identical to such a sequence. However, the present invention contemplates fragments that comprise about 7, 8, 9, 10, 11, 12, 13, 14, 15, 16, 17, 18, 19, 20, 21, 23, 25, 30, 35, 40, 45, 50, 55, 60, 65, 70, 75, 80, 85, 90, 95, 100, 120, 150, 200, 250, 300, 350, 400, 450, 500, 550, 600, 650, 670, 680, 690, 691 amino acids, or any number therein between. Further, the PCSK9 polypeptide or polypeptide fragment may be defined as comprising a range of sizes encompassed by any two of the values listed above, or any two values therein between.

The PCSK9 polypeptide or polypeptide fragment may include polypeptides that are substantially identical to SEQ ID NO:1 or a fragment thereof. Sequences are considered "substantially identical" when at least about 70% or more of the amino acids are identical over at least seven consecutive amino acids of SEQ ID NO:1. For example, the present invention contemplates PCSK9 polypeptides or polypeptide fragments that are at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 99.99% identical over a length as defined above. Further, the PCSK9 polypeptide or polypeptide fragment provided by the present invention may be defined as comprising a range of sequence identity as defined by any two of the values listed or any two values therein between.

Any method known in the art may be used for determining the degree of identity between polypeptides sequences. For example, but without wishing to be limiting, a sequence search method such as BLAST (Basic Local Alignment Search Tool; (Altschul S F, Gish W, Miller W, Myers E W, Lipman D J (1990) J Mol Biol 215, 403 410) can be used according to default parameters as described by Tatiana et al., FEMS Microbial Lett. 174:247 250 (1999), or on the National Center for Biotechnology Information web page at ncbi.nlm.gov/BLAST/, for searching closely related sequences. BLAST is widely used in routine sequence alignment; modified BLAST algorithms such as Gapped BLAST, which allows gaps (either insertions or deletions) to be introduced into alignments, or PSI-BLAST, a sensitive search for sequence homologs (Altschul et al., Nucleic Acids Res. 25:3389 3402 (1997); or FASTA, which is available on the world wide web at ExPASy (EMBL—European Bioinformatics Institute).

In an embodiment, which is not meant to be limiting in any manner, the PCSK9 polypeptide or polypeptide fragment comprises Serine 47, Serine 688 or both of SEQ ID NO:1. Further, it is also contemplated that Serine 47, Serine 688 or both may be phosphorylated in a PCSK9 polypeptide or polypeptide fragment.

In addition to comprising polypeptides that are unphosphorylated and/or phosphorylated, the PCSK9 polypeptide or polypeptide fragment also may comprise other variants or derivatives. A "variant" or "derivative" is a polypeptide or peptide containing additional chemical or biochemical moieties that may or may not be part of the naturally occurring PCSK9 protein. Variants and derivatives include polypeptides and peptides wherein one or more of the amino acids defined therein are subject to sulfation, glycosylation, ribosylation, or any other post-translational modification known in the art. Further, variants and derivatives are meant to include polypeptides in which the amino-terminus and/or the carboxy-terminus and/or one or more amino acid side chain has been modified with a desired chemical substituent group, as well as cyclic polypeptides, polypeptides fused to heterologous proteins or carriers, for example, but not limited to antibodies, lipophilic moieties, hydrophilic polymers and the like.

Examples of chemical substituent groups that may be used to produce variant or derivative polypeptides include, but are not limited to, alkyl, cycloalkyl and aryl groups; acyl groups, including alkanoyl and aroyl groups; esters; amides; halogens; hydroxyls; carbamyls, and the like. The substituent group may also be a blocking group such as Fmoc (fluorenylmethyl-O—CO—), carbobenzoxy (benzyl-O—CO—), monomethoxysuccinyl, naphthyl-NH—CO—, acetylaminocaproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

The PCSK9 polypeptide or fragments thereof can be prepared by any suitable method known in the art. For example, but without wishing to be limiting, the protein or fragments thereof may be purified from cell extracts using recombinant techniques. Shorter sequences can also be chemically synthesised by methods known in the art including, but not limited to, exclusive solid phase synthesis, partial solid phase synthesis, fragment condensation or classical solution synthesis (Merrifield (1963) J. Am. Chem. Soc. 85:2149; Merrifield (1986) Science 232:341). The polypeptides of the present invention may be purified using standard techniques such as, for example, but not limited to chromatography (e.g. ion exchange, affinity, size exclusion chromatography, or high performance liquid chromatography (HPLC)), centrifugation, differential solubility, or by any other suitable technique familiar to a worker skilled in the art.

As noted above, the PCSK9 polypeptide or polypeptide fragment also may be produced by recombinant techniques. Typically, this involves transformation (including one or more of transfection, transduction, and/or infection) of a suitable host cell with an expression vector comprising a polynucleotide encoding the protein or polypeptide.

The PCSK9 polypeptide or polypeptide fragment thereof may be fused to a heterologous protein or polypeptide sequence. The production of PCSK9 polypeptide or fragments thereof as fusion proteins may simplify or improve protein purification, or may facilitate detection of the polypeptide. For example, but without wishing to be limiting in any manner, the fusion protein may be an immunoglobulin Fc domain. In such a case, the resultant PCSK9 polypeptide or polypeptide fragment fusion protein may be readily purified using a protein A column. In another non-limiting example, the PCSK9 polypeptide or polypeptide fragment thereof may be fused to glutathione S-transferase (GST) and the fusion protein purified on a glutathione column. Other non-limiting examples of fusion domains include histidine tags (purification on $Ni^{2+}$ resin columns), a FLAG-tag (purification by anti-FLAG affinity chromatography), or to biotin (purification on streptavidin columns or with streptavidin-labelled magnetic beads). As would be readily recognized by a person of skill in the art, a linker (or "spacer") peptide or other chemical linker may be added between the PCSK9 polypeptide or fragment thereof and the fusion domain to ensure that the proteins fold independently. Once the fusion protein has been purified, the fusion domain may be removed by site-specific cleavage using a suitable chemical or enzymatic method known in the art.

The present invention also includes nucleic acids encoding PCSK9 polypeptide or polypeptide fragments as defined above. The present invention is further directed to a nucleotide construct comprising a nucleic acid encoding a PCSK9 polypeptide or polypeptide fragment thereof, as described above, operatively linked to one or more regulatory elements or regulatory regions. By "regulatory element" or "regulatory region", it is meant a portion of nucleic acid typically, but not always, upstream of a gene, and may be comprised of either DNA or RNA, or both DNA and RNA. Regulatory elements may include those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. By a nucleotide sequence exhibiting regulatory element activity it is meant that the nucleotide sequence when operatively linked with a coding sequence of interest functions as a promoter, a core promoter, a constitutive regulatory element, a negative element or silencer (i.e. elements that decrease promoter activity), or a transcriptional or translational enhancer.

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

Regulatory elements as used herein, also includes elements that are active following transcription initiation or transcription, for example, regulatory elements that modulate gene expression such as translational and transcriptional enhancers, translational and transcriptional repressors, and mRNA stability or instability determinants. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, may be operatively associated (operatively linked) with heterologous regulatory elements or promoters in order to modulate the activity of the heterologous regulatory element. Such modulation includes enhancing or repressing transcriptional activity of the heterologous regulatory element, modulating post-transcriptional events, or both enhancing/repressing transcriptional activity of the heterologous regulatory element and modulating post-transcriptional events. For example, one or more regulatory elements, or fragments thereof, may be operatively associated with constitutive, inducible, tissue specific promoters or fragment thereof, or fragments of regulatory elements, for example, but not limited to TATA or GC sequences may be operatively associated with the regulatory elements of the present invention, to modulate the activity of such promoters within plant, insect, fungi, bacterial, yeast, or animal cells.

There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within a plant as well.

By "promoter" it is meant the nucleotide sequences at the 5' end of a coding region, or fragment thereof that contain all the signals essential for the initiation of transcription and for the regulation of the rate of transcription. There are generally two types of promoters, inducible and constitutive promoters. If tissue specific expression of the gene is desired, for example seed, or leaf specific expression, then promoters specific to these tissues may also be employed.

An inducible promoter is a promoter that is capable of directly or indirectly activating transcription of one or more DNA sequences or genes in response to an inducer. In the absence of an inducer the DNA sequences or genes will not be transcribed. Typically the protein factor that binds specifically to an inducible promoter to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus.

A constitutive promoter directs the expression of a gene throughout the various parts of an organism and/or continuously throughout development of an organism. Any suitable constitutive promoter may be used to drive the expression of the fragment of PCSK9 polypeptide within a transformed cell, or all organs or tissues, or both, of a host organism. Examples of known constitutive promoters include those associated with the CaMV 35S transcript. (Odell et al., 1985, *Nature*, 313: 810-812). In cases where it may be desirable to produce the PCSK9 polypeptide or fragment thereof in plants, plant promoters, such as, but not limited to those associated with the rice actin 1 (Zhang et al, 1991, *Plant Cell*, 3: 1155-1165) and triosephosphate isomerase 1 (Xu et al, 1994, *Plant Physiol.* 106: 459-467) genes, the maize ubiquitin 1 gene (Comejo et al, 1993, *Plant Mol. Biol.* 29: 637-646), the *Arabidopsis* ubiquitin 1 and 6 genes (Holtorf et al, 1995, *Plant Mol. Biol.* 29: 637-646), and the tobacco translational initiation factor 4A gene (Mandel et al, 1995 *Plant Mol. Biol.* 29: 995-1004) may be used.

The term "constitutive" as used herein does not necessarily indicate that a gene is expressed at the same level in all cell types, but that the gene is expressed in a wide range of cell types, although some variation in abundance is often observed.

The gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3 prime end of the mRNA precursor.

The gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

The present invention further includes vectors comprising the nucleic acids as described above. Suitable expression vectors for use with the nucleic acid sequences of the present invention include, but are not limited to, plasmids, phagemids, viral particles and vectors, phage and the like. For insect cells, baculovirus expression vectors are suitable. For plant cells, viral expression vectors (such as cauliflower mosaic virus and tobacco mosaic virus) and plasmid expression vectors (such as the Ti plasmid) are suitable. The entire expression vector, or a part thereof, can be integrated into the host cell genome.

Those skilled in the art will understand that a wide variety of expression systems can be used to produce the PCSK9 polypeptide or polypeptide fragment. With respect to the in vitro production, the precise host cell used is not critical to the invention. The PCSK9 polypeptide or polypeptide fragment thereof can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, Hek 293, or HeLa cells; insect cells; or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley & Sons, New York; and various expression vectors may be chosen from those provided, e.g., in Cloning Vectors: A Laboratory Manual (Pouwels et al., 1985, Supp. 1987) and by various commercial suppliers.

In addition, a host cell may be chosen which modulates the expression of the inserted sequences, or modifies/processes the gene product in a specific, desired fashion. Such modifications (e.g., glycosylation) and processing (e.g., cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed PCSK9 polypeptide.

The present invention further provides pharmaceutical compositions comprising PCSK9 polypeptide or a fragment thereof and a pharmaceutically acceptable diluent, excipient or vehicle. Pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

Administration of the pharmaceutical compositions of the present invention may be via a number of routes depending upon whether local or systemic treatment is desired and whether a specific area is to be treated. Accordingly, the composition may be administered locally to the area to be treated. Further, the present invention contemplates parenteral administration including, but not limited to intravenous, intra-arterial, subcutaneous, intraperitoneal or intramuscular injection. Preferably, the PCSK9 polypeptide or polypeptide fragment is administered by intravenous injection.

As described above, the compositions of the present invention may be delivered in combination with a pharmaceutically acceptable vehicle. Preferably, such a vehicle enhances the stability and/or delivery properties. Examples may include liposomes, microparticles or microcapsules. In various embodiments of the invention, the use of such vehicles may be beneficial in achieving sustained release of the active component. The composition may also be delivered or formulated for timed-release, where the PCSK9 polypeptide or polypeptide fragments are released in a time-dependent manner. See WO 02/45695; U.S. Pat. No. 4,601,894; U.S. Pat. No. 4,687,757, U.S. Pat. No. 4,680,323, U.S. Pat. No. 4,994,276, U.S. Pat. No. 3,538,214, US (which are incorporated herein by reference) for several non-limiting examples of time-release formulations that may be used to assist in the time controlled release of PCSK9 polypeptides or fragments thereof within aqueous environments.

When formulated for parenteral injection, the pharmaceutical compositions are preferably used in the form of a sterile solution, containing other solutes, for example, enough saline or glucose to make the solution isotonic.

The dosage requirements for the pharmaceutical compositions vary with the particular compositions employed, the route of administration and the particular subject being treated. Typically, but not always, treatment will generally be initiated with small dosages less than the maximum or optimum dose of each compound. Thereafter the dosage is increased until the optimum effect under the circumstances is reached. In general, the pharmaceutical compositions are administered at a concentration that will generally afford effective results without causing any harmful or deleterious side effects. Administration can be either as a single unit dose, a sustained delivery dose or, if desired, the dosage can be divided into several doses that are administered at suitable times throughout the day.

The present invention also contemplates administration of a nucleotide sequence encoding a PCSK9 polypeptide or fragment thereof, which then expresses the encoded product in vivo. This may be accomplished via by various "gene therapy" methods known in the art. General methods of administering proteins or protein fragments are known in the art. Gene therapy includes both ex vivo and in vivo techniques. Thus, host cells may be genetically engineered ex vivo with a polynucleotide, with the engineered cells then being provided to a subject to be treated as described above.

Alternatively, cells can be engineered in vivo by administration of a PCSK9 polypeptide or fragment thereof, or a nucleotide sequence encoding the same using techniques known in the art, for example, by direct injection of a "naked" polynucleotide (Feigner and Rhodes, (1991) Nature 349:351-352; U.S. Pat. No. 5,679,647) or a polynucleotide formulated in a composition with one or more other agents which facilitate uptake of the polynucleotide by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the polynucleotide with lipids, cell-surface receptors or transfecting agents; by encapsulation of the polynucleotide in liposomes, microparticles, or microcapsules; by administration of the polynucleotide linked to a peptide which is known to enter the nucleus; or by administration of the polynucleotide linked to a ligand subject to receptor-mediated endocytosis (see, for example, Wu and Wu, (1987) J. Biol. Chem. 262:4429-4432), which can be used to target cell types specifically expressing the receptors.

In another alternative, a protein/fragment-ligand complex may be formed in which the ligand comprises a fusogenic viral peptide to disrupt endosomes, allowing the PCSK9 polypeptide or fragment thereof to avoid lysosomal degradation; or the protein or fragment thereof may be targeted for cell specific uptake and expression in vivo by targeting a specific receptor (see, for example, International Patent Applications WO 92/06180, WO 92/22635, WO92/20316, WO93/14188 and WO 93/20221). The present invention also contemplates the intracellular introduction of the polynucleotide and subsequent incorporation within host cell DNA for expression by homologous recombination (see, for example, Koller and Smithies (1989) Proc. Natl. Acad. Sci. USA 86:8932-8935; Zijlstra et al. (1989) Nature 342:435-438).

As described above, the polynucleotide may be incorporated into a suitable expression vector. A number of vectors suitable for gene therapy applications are known in the art (see, for example, Viral Vectors: Basic Science and Gene Therapy, Eaton Publishing Co. (2000)). In one such embodiment, which is not meant to be limiting in any manner, the expression vector may be a plasmid vector. Plasmid DNA typically does not integrate into the genome of the host cell, but is maintained in an episomal location as a discrete entity eliminating genotoxicity issues that chromosomal integration may raise. A variety of plasmids are available commercially and include those derived from *Escherichia coli* and *Bacillus subtilis*, with many being designed particularly for use in mammalian systems. Examples of plasmids that may be used in the present invention include, but are not limited to, the eulcaryotic expression vectors pRc/CMV (Invitrogen), pCR2.1 (Invitrogen), pAd/CMV and pAd/TR5/GFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or pVAX (Invitrogen).

Alternatively, the expression vector may be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous genes in vivo, particularly into humans. These vectors provide efficient delivery of genes into cells, and the transferred polynucleotides are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumour virus. Specific retroviruses include pLJ, pZIP, pWE and pEM, which are well known to those skilled in the art.

The polynucleotide may be incorporated into the vector under the control of a suitable promoter that allows for expression of the encoded polypeptide in vivo. Suitable promoters which may be employed include, but are not limited to, adenoviral promoters, such as the adenoviral major late promoter, the E1A promoter, the major late promoter (MLP) and associated leader sequences or the E3 promoter; the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTR; the histone, pol III, and (α-actin promoters; B19 parvovirus promoter; the SV40 promoter; and human growth hormone promoters). The promoter also may be the native promoter for the gene of interest. The selection of a suitable promoter will be dependent on the vector, the host cell and the encoded protein and is considered to be within the ordinary skills of a worker in the art.

The development of specialised cell lines (also referred to as "packaging cells") that produce only replication-defective retroviruses has increased the utility of retroviruses for gene therapy, and defective retroviruses are well characterised for use in gene transfer for gene therapy purposes (for a review see Miller, A. D. (1990) Blood 76:271). Thus, recombinant retrovirus can be constructed in which part of the retroviral coding sequence (gag, pol, env) has been replaced by subject polynucleotide and renders the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.), J. Wiley & Sons, (1989), Sections 9.10-9.14 and other standard laboratory manuals. Examples of suitable packaging virus lines for preparing both ecotropic and amphotropic retroviral systems include Crip, Cre, 2 and Am. Other examples of packaging cells include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, Vol. 1, pgs. 5-14 (1990).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86:9079-9083; Julan et al. (1992) J. Gen Virol 73:3251-3255; and Goud et al. (1983) Virology 163: 251-254); or coupling cell surface receptor ligands to the viral env proteins (Neda et al. (1991) J Biol Chem 266:14143-14146). Coupling can be in the form of the chemical cross-linking with a protein or other variety (for example, lactose to convert the env protein to an asialoglycoprotein), as well as by generating fusion proteins ((for example, single-chain antibody/env fusion proteins). This technique, while useful to limit or otherwise direct the infection to certain tissue types, may also be used to convert an ecotropic vector in to an amphotropic vector.

Moreover, use of retroviral gene delivery can be further enhanced by the use of tissue- or cell-specific transcriptional regulatory sequences which control expression of the polynucleotides contained in the vector.

Another viral vector useful in gene therapy techniques is an adenovirus-derived vector. The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (for example, Ad2, Ad3, Adz etc.) are well known to those skilled in the art. Recombinant adenoviruses can be advantageous in certain circumstances in that they can be used to infect a wide variety of cell types. Furthermore, the virus particle is relatively stable and amenable to purification and concentration, and as above, can be modified so as to affect the spectrum of infectivity. Additionally, introduced adenoviral DNA (and foreign DNA contained therein) is not always integrated into the genome of a host cell but can remain episomal, thereby avoiding potential problems that can occur as a result of insertional mutagenesis in situations where introduced DNA becomes integrated into the host genome (for example, retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and contemplated by the present invention are deleted for all or parts of the viral E2 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109-127).

Generation and propagation of replication-defective human adenovirus vectors usually requires a unique helper cell line. Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus, i.e. that provide, in trans, a sequence necessary to allow for replication of a replication-deficient virus. Such cells include, for example, 293 cells, Vero cells or other monkey embryonic mesenchymal or epithelial cells. The use of non-human adenovirus vectors, such as porcine or bovine adenovirus vectors is also contemplated. Selection of an appropriate viral vector and helper cell line is within the ordinary skills of a worker in the art.

In one embodiment of the present invention, the gene therapy vector is an adenovirus-derived vector.

When the components of the kit are provided in one or more liquid solutions, the liquid solution can be an aqueous solution, for example a sterile aqueous solution. In this case the kit may further comprise a syringe, pipette, eye dropper, catheter, loadable osmotic pump or other such apparatus, from which the protein, fragment or composition comprising the same may be administered and/or delivered to a patient or subject.

The components of the kit may also be provided in dried or lyophilised form and the kit can additionally contain a suitable solvent for reconstitution of the dry or lyophilised components. Irrespective of the number or type of containers, the kits of the invention also may comprise an instrument for assisting with the administration of the composition to a patient.

Methods

The present invention also contemplates a method of modulating LDLR degradation comprising administering a compound as described herein that modulates LDLR degradation in a cell, cell culture or subject. The present invention also contemplates a method of modulating LDLR degradation comprising administering a PCSK9 polypeptide or polypeptide fragment to a cell, cell culture or subject to affect LDLR degradation. Further, there is provided a method of protecting LDLR from degradation comprising administering an unphosphorylated PCSK9 polypeptide or polypeptide fragment of SEQ ID NO:1 that comprises Serine 47, a phosphorylated PCSK9 polypeptide or polypeptide fragment, for example, but not limited to SEQ ID NO:1 that comprises a phosphorylated or unphosphorylated Serine 688 to a cell, cell culture or subject to protect LDLR degradation. In still a further embodiment, there is provided a method of accentuating LDLR degradation comprising administering a phosphorylated PCSK9 polypeptide or polypeptide fragment of SEQ ID NO:1 that comprises phosphoSerine 47. In a further embodiment, there is also provided a method of increasing LDLR levels comprising administering a serine kinase inhibitor to a cell, cell culture or subject to increase LDLR levels. In a preferred embodiment, the serine kinase inhibitor is a broad spectrum serine kinase inhibitor, for example, but not limited to staurosporine. Other methods as defined above are also contemplated by the present invention.

The invention will now be described in detail by way of reference only to the following non-limiting examples.

Example 1

Materials and Methods

The cDNA of human PCSK9 was cloned into the pIRES2-EGFP with or without a CterminalV5 tag as described [2]. Mutations were introduced by site directed mutagenesis as described [49]. The antibody, anti-hPCSK9 Ab, used for immunoprecipitation of endogenous or untagged recombinant PCSK9 was raised in rabbits by cDNA vaccination with the mammalian expression vector pcDNA3 into which the cDNA for human PCSK9 had been inserted [50]. The anti-LDLR antibody was purchased from Research Diagnostics. The anti-V5 mouse monoclonal antibody used for immunoprecipitation of V5-tagged recombinant PCSK9 was from Invitrogen (Burlington, Ontario, Canada) and the goat anti-C-terminal PCSK9 Ab used for immunoblotting from Imgenex (San Diego, Calif., USA). Secondary antimouse and anti-rabbit HRP antibodies were from Amersham and the secondary anti-goat HRP antibody was from Santa Cruz Biotechnology (Santa Cruz, Calif., USA).

Cell Culture, Transfection and Sample Collection

HepG2, Huh7, Hek293 and CHOK1 cells were grown at 37° C. in DMEM+10% FBS+gentamycin (28 µg/ml). Cells ($3 \times 10^5$) were transfected with a plasmid expression vector for human PCSK9 (hPCSK9; 1.5 µg) as described using Lipofectamine 2000 (Invitrogen) in a 1:1 ratio to cDNA [2]. Spent media from untransfected and transfected cells were collected in the presence of a general protease inhibitor cocktail (Roche) and 200 µM sodium orthovanadate (a phosphatase inhibitor; Sigma Aldrich, Oakville, Ontario, Canada) and centrifuged at 13,000×g for 3 min to remove suspended cells and debris. Cell were lysed in 1XRIPA buffer [50 mM Tris (pH 7.6), 150 mM NaCl, 1% (v/v) NP-40, 0.5% (w/v) DOC, 0.1% (w/v) SDS] in the presence of inhibitors, as above. Lysates were rotated at 4° C. for 30 min, centrifuged at 13,000×g for 3 min and supernatants collected. Protein concentrations in total cell lysates (TCL) were determined by the Bradford dye-binding method using Bio-Rad's Protein Assay Kit.

Immunoprecipitation, Immunoblotting and Radiolabelling

Iumunoprecipitations were carried out in 1× Tris buffered saline+0.1% Tween-20 (TBS-Tw) with anti-hPCSK9 Ab (dilution 1:500), preimmune sera (dilution 1:500) or anti-V5 antibody (⅕₀₀) and 30 µl of Protein-A agarose (Sigma-Aldrich) overnight at 4° C. Immunoprecipitates were washed 4× with 1 ml TBS-Tw and fractionated through a 12% polyacrylainde gel. Proteins were electroblotted onto nitrocellulose and immunoblotted following a standard protocol. The primary anti-C-terminal PCSK9 and anti-V5 Abs were used at 1/2000 dilutions and the secondary Abs at 1/5000 dilutions. Immunoblots were revealed by chemiluminescence using Western Lightening Plus (Perkin-Elmer) on X-OMAT film (Kodak). The signal was quantified by densitometry using Syngene's Chemigenius 2XE imager and GeneTool software.

Untransfected and transfected HepG2 and Huh7 cells were grown to confluence as above. Prior to radiolabeling cells were incubated for 4 hours in serum-free DMEM without sodium phosphate (Invitrogen) or methionine/cysteine (Met/Cys) free DMEM (Invitrogen) and then incubated for 16 hrs in the same media in the presence of either 250 µCi 32P-orthophosphate or 250 µCi 35S-Met/Cys. Media and TCLs were harvested and immunoprecipitated as described above. Samples were fractionated through a 12% SDSPAGE. Following electrophoresis gels were dried and visualized by phosphoimaging using a Typhoon Imager. Signals were quantified using ImageQuant 5.2 software using the integer integration method when comparing samples within a lane and, for samples between lanes, by volume quantitation as recommended.

Mass Spectrometry Analyses

Spent media from cell cultures of HepG2, Huh7, Hek293 and CHOK1 cells untransfected and transfected with a hPCSK9 expression vector were collected and immunoprecipitated as above for time-of-flight mass spectral (TOF-MS) analysis of immunocaptured PCSK9 as previously described, except that following immunoprecipitation, the antibody:antigen complex was eluted from the Protein-A beads by incubation in 2×150 μL 0.1 M glycine (pH 2.8) for 10 min at RT [4]. Supernatants were collected, combined and neutralized with 30 μL 1M Tris-HCl (pH 9.0), concentrated 20× with an Amicon Ultra YM10 Centricon (Millipore Corp) and retentates equilibrated in 0.1% trifluoroacetic acid (TFA). Ten microliters of the sample was applied to a Gold ProteinChip Array (Ciphergen Biosystems Inc, BioRad) and air-dried. One microliter of saturated 3,5-dimethoxy-4-hydroxycinnamic acid (SPA) in 50% (v/v) acetonitrile (ACN)+0.5% (v/v) TFA was added and samples analysed by TOF-MS in a Ciphergen Protein Biology System II. Analyses represent an average of 100 shots and masses were externally calibrated with All-in-1 Protein Standards (Ciphergen Biosystems Inc, BioRad). All data were normalized for total ion current and peak areas calculated using the indirect method (with a bracket height of 0.4 and width expansion factor of 2) contained within Ciphergen's ProteinChip Software 3.1.

Dephosphorylation

Enzymatic dephosphorylation was carried out by incubating immunoprecipitates in the presence of 10 units (except where indicated) of shrimp alkaline phosphatase (Fermentas, Burlington, Ontario, Canada) in provided reaction buffer system for 30 min at 37° C. with agitation.

Trypsin Digestion

Trypsin digestion was carried out by incubating immunoprecipitates in the presence of 6 ng/μl trypsin (Roche) in 25 mM $NH_4HCO_3$ and 1% (v/v) ACN overnight at 37° C. with agitation.

Statistical Analyses

All results are expressed as mean±standard error (SE), except where indicated. Data were analyzed using GraphPad Prism 5.0 statistical software with significance defined as $p<0.05$.

Example 2

The Secreted Propeptide of PCSK9 is Phosphorylated in a Cell-Type Specific Manner We examined the heterogeneity of the molecular mass of the propeptide of endogenous PCSK9 in the media of HepG2 cells by MS analyses of immunoprecipitates with immune (I) sera directed against PCSK9 or preimmune (PI) sera (FIGS. 2A and B, respectively). Panel A illustrates the two molecular forms of secreted PCSK9 propeptide, the peak at 13834.6 Da is due to sulfation at Tyr38 ($SO_4^{2-}$-Y38; calculated mass 13835.5Da with modification at pyroGlu31) [5] while the peak at 13915.5 Da is due to $SO_4^{2-}$-Y38 with an additional modification of ~80Da. Panel B shows a non-specific peak interacting with the PI serum at 14417 Da. To examine whether PCSK9 propeptide heterogeneity was due to phosphorylation, immunoprecipitates were incubated in the presence (panels C and D) of SAP. Following SAP incubation, PCSK9 propeptide heterogeneity was lost and a single peak corresponding to its sulfated molecular form was resolved at 13834.5 Da (panel C) while the non-specific peak was unaffected by this treatment (panel D). Heterogeneity of the propeptide of PCSK9 in the absence of SAP indicated that not all secreted propeptide is phosphorylated (FIG. 2A). This partial modification has been reported for a number of other secreted phosphoproteins such as insulin growth factor binding proteins (IGFBPs) and osteopontin [25], and is unlike the complete modification reported for phosphoproteins secreted from mammary and salivary glands [25]. Interestingly, MS analyses of the PCSK9 propeptide immunoprecipitated from HepG2 TCLs did not show intracellular phosphorylation of the PCSK9 propeptide (data not shown) suggesting that this phosphorylation occurs just prior to PCSK9 secretion, as we had previously documented for its sulfation at Tyr38 [4,5].

Using the same technique as above, we next examined propeptide phosphorylation from the spent media of several cell lines transfected with the expression vector for a C-terminal V5-tagged wild type hPCSK9 [hPCSK9(WT)-V5], including the human liver cell lines HepG2 and Huh7, the human embryonic kidney cell line HEK293 and the Chinese hamster ovary cell line CHOK1 (FIG. 2E-H, respectively). These cell lines are the most commonly used to study PCSK9 biosynthesis and for studying PCSK9-dependent LDLR degradation [5, 10, 26]. The ratio of secreted propeptide phosphorylation, assessed by determining the ratio between unphosphorylated but sulfated propeptide to phosphorylated propeptide signal ($SO_4^{2-}/PO_4^{2-}$) as area under the peak was similar between transduced hPCSK9(WT)-V5 expressed in HepG2 cells (FIG. 2E; 46/54±0.02, n=5) and that produced endogenously (FIG. 2A; 55/45±0.11, p=0.16, n=7). However, the ratio of unphosphorylated but sulfated propeptide to phosphorylated propeptide from the media of Huh7 cells transfected with hPCSK9(WT)-V5 was 30/70±0.04 suggesting that significantly more of the PCSK9 propeptide is secreted as a phosphoprotein from this cell line (FIG. 2F; p=0.003, n=5). In contrast, the HEK293 cell line expressing hPCSK9(WT)-V5 secreted only 23±0.02% (n=3) of PCSK9 propeptide in its phosphorylated form and significantly less than both liver cell lines; p<0.0001 for both (FIG. 2G). No phosphorylation of PCSK9 propeptide was detected in the CHOK1 cell line (FIG. 2H, n=3). These results demonstrate cell-type specificity of phosphorylation of the PCSK9 propeptide, with the ratio of unphosphorylated to phosphorylated differing significantly among the cell lines examined. This may be due, in part, to cell-specific kinase and/or phosphatase activities and/or differing levels therein. Although sulfated and phosphorylated peptides <8000 Da differ in their detection efficiency by MS, this difference is lost when comparing like molecules that are >8000 Da [27,28]. Therefore the measure of the area under the peak for the unphosphorylated and sulfated PCSK9 propeptide (13835.5 Da) to the phosphorylated and sulfated PCSK9 propeptide (13,915.5 Da) is a valid comparison. As well, a minor but specific band is present in these spectra at ~14150 Da (FIGS. 2E and F) and ~14070 Da (FIGS. 2G and H) that represents alternative signal peptidase cleavage site following Ala28 (ACS; calculated mass 14159.8 Da for $SO_4^{2-}-PO_4^{2-}$ propeptide and 14079.8 Da for $SO_4^{2-}$ propeptide) instead of Ala30 (FIG. 2E-H). Indeed, SignalP 3.0 Server (a signal peptide prediction program) predicted the primary signal peptide site as ARA30↓QE and a secondary signal peptide site as A28↓RAQE.

Example 3

Serine 47 is the Site of Phosphorylation in the Propeptide of PCSK9

Figure 3:
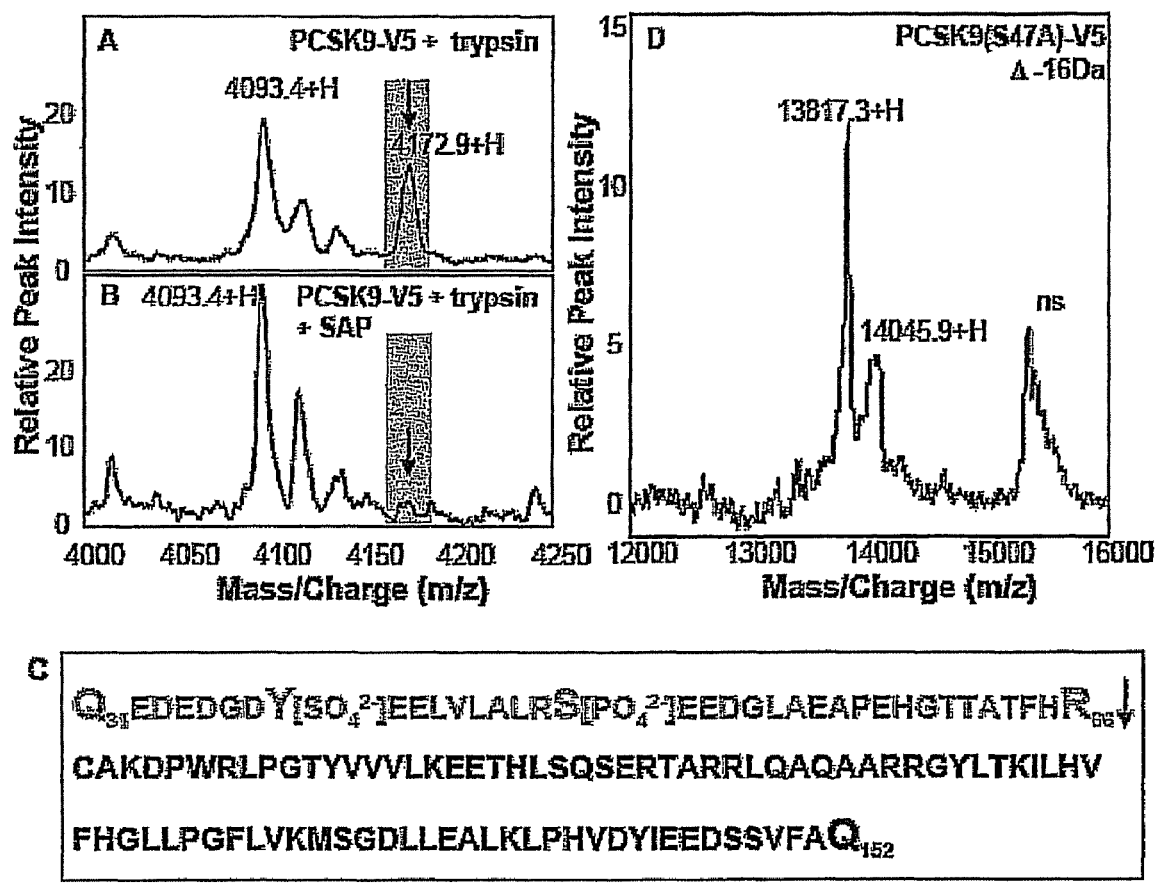
FIG. 3A-D shows mass spectral analysis of PCSK9-propeptide tryptic digests and phosphorylation site PCSK9-propeptide variant. A and B represent TOF-MS analyses of the tryptic peptides from the immunoprecipitates of the propeptide of V5-tagged PCSK9 from the media of transfected and overexpressing Huh7 cells in the absence (A) and presence of SAP (B). Panel C illustrates the amino acid sequence of the propeptide of PCSK9 (residues 31-152 of SEQ ID NO: 1). pyroQ31, $SO_4^{2-}$Y38 and $PO_4^{2-}$ S47 are shown. The phosphorylated tryptic peptide is highlighted by gray boxes in panels A and B and the corresponding amino acid sequence highlighted with grey font and is shown in the first line of panel C. Panel D represents MS analyses of the molecular form of the propeptide variant (S47A) of V5-tagged PCSK9 immunoprecipitates from the media of transfected and overexpressing Huh7 cells. Analyses were conducted on at least 3 independent experiments. ns; non-specific.

To define the site of phosphorylation in the PCSK9-propeptide we immunoprecipitated hPCSK9(WT)-V5 from transfected HepG2 cells, treated half with SAP and then digested with trypsin (FIG. 3). Mass spectral analyses of the tryptic peptides incubated in the absence or presence of SAP revealed a peptide that shifted by 79.5 Da, corresponding to pyroGlu31-Arg66 within the propeptide (FIG. 3A: observed 4172.9 Da versus calculated 4174.2 Da and panel B: observed 4093.4 Da versus calculated 4094.2 Da, respectively). Ser47 within this peptide (panel E) exhibits a minimal consensus site (S47EED) for two kinases demonstrated to act on secretory proteins; golgi casein kinase (GCK; consensus site SXE/S(P))[29] and casein kinase II (CKII; consensus site S/TXXE/D)[30]. Phosphorylation of Ser47 was confirmed by SDM (FIG. 3): when this residue was mutated to Ala and the construct (hPCSK9(S47A)-V5) transduced into Huh7 cells, the propeptide was no longer phosphorylated, showing a single peak of 13817.3 Da, corresponding to $SO_4^{2-}$ propeptide (calculated size 13819.5 Da; FIG. 3C).

Example 4

Figure 4:
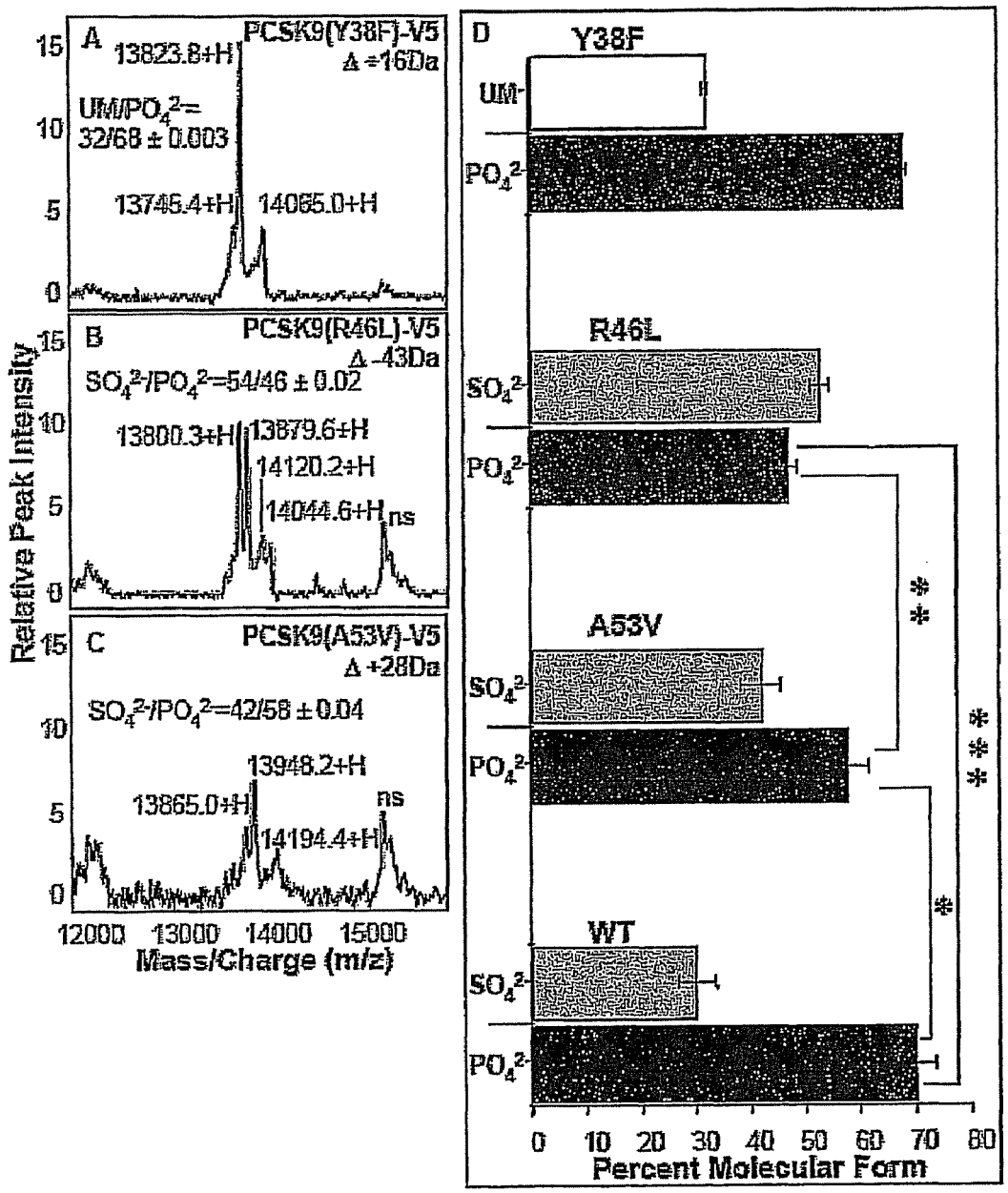
FIG. 4A-D shows mass spectral analysis of immunoprecipitated PCSK9 propeptide from the media of transfected Huh7 cells overexpressing V5-tagged PCSK9 variants. A-C represent TOF-MS analyses of the propeptide of V5-tagged PCSK9 variants as labeled from the media of transfected and overexpressing Huh7 cells. For each variant the change in molecular mass due to the specific amino acid change is show as ΔDa. Panel D shows a graphic representation of the data incorporating results from analyses of the propeptide of V5-tagged wild type PCSK9. The ratio of unmodified (UM; white bar) or sulfated ($SO_4^{2-}$; grey bars) to sulfated and phosphorylated ($PO_4^{2-}$; black bars), calculated as AUP as described in the Examples (see Materials and Methods), is shown±standard error. T-tests were carried out to compare significant changes in phosphorylation of the propeptide of PCSK9 between variants. Analyses were conducted on at least 3 independent experiments. ns; non-specific. *p<0.05, p<0.005, *p<0.0005.

Phosphorylation of Ser47 in the Propeptide of PCSK9 is Decreased by the Naturally Occurring R46L and A53V PCSK9 Variants We next examined the effect of several hPCSK9-V5 variations on the phosphorylation of secreted propeptide, namely the Y38F variation preventing sulfation of the prodomain, the common naturally-occurring A53V variation that has no significant effect on plasma cholesterol levels and the R46L variation, a naturally-occurring variant associated with hypocholesterolemia [31] and reduced plasma PCSK9 [22]. As shown in FIG. 4, panel A, mutating the site of propeptide sulfation [hPCSK9(Y38F)-V5] did not significantly affect PCSK9 propeptide phosphorylation in comparison to hPCSK9(WT)-V5 (FIG. 4D, p=0.67), as assessed by comparing AUP for the unphosphorylated versus phosphorylated signals. In contrast, the level of propeptide phosphorylation for both the R46L and the A53V PCSK9 variants were reduced by 34% (p=0.0001) and 17% (p=0.04) respectively, in comparison to hPCSK9(WT)-V5 (FIG. 4B-D). In addition, the level of phosphorylation of the R46L variant (46±0.2%, n=6) was significantly less than the A53V PCSK9 variant (58±0.4%, n=5, p=0.01) (FIG. 4D). Therefore, replacement of the n−1 basic residue Arg by Leu, decreases the rate of phosphorylation at Ser47, indicating the importance of this residue in the consensus site or conformation recognition by its cognate kinase. As well, the reduced phosphorylation of the A53V variant in comparison to wild type also indicates that residues downstream of Ser47 may also impact its PTM. In a previous study, we observed that individuals heterozygous for the PCSK9(R46L) variant have reduced circulating PCSK9 when compared to individuals carrying the normal PCSK9 alleles [22].

Site-directed mutagenesis shows consensus sequence site of golgi casein-like kinase (GCK; SXE/S(p)) for propeptide phosphorylation. To determine the consensus site of phosphorylation within the propeptide of PCSK9, IPs of V5-tagged recombinant PCSK9 from transfected Huh7 cells were analysed by MS (FIG. 5). Below each spectra is the observed and calculated (in brackets) molecular masses for each mutant in its $SO_4^{2-}$ and $SO_4^{2-}$ $PO_4^{2-}$ forms, as well as the major molecular form observed. Mutations E48A and E48D did not affect phosphorylation (panels C and D), nor did D50A and D50E (panels G and H). However mutations E49A and E49D prevented phosphorylation of the propeptide (panels E and F). The requirement of a Glu at n+2 (Panel C) and the inability for Asp (Panel D) to mimic its effect, is a strict requirement for phosphorylation by GCK, SXE/S(p) [29], and not CKII whose consensus site requires n+3 E or D (SXXE/D).

A cleaved PCSK9 propeptide product was detected in the media of Huh7 cells transfected with the E49A PCSK9 variant at 11738.2 Da (FIG. 5E, inset), due to cleavage following Ser47 and corresponded to 13% of the AUP for total propeptide (observed ΔDa Q31-Ser47 2026.1 versus calculated 2044.1 Da), but not with the E49D variant (FIG. 5F inset). This product was also observed in immunoprecipitates from the media of cells expressing the R46L variant and corresponded to 5% of the AUP for total propeptide (FIG. 5B, inset) (observed ΔDa Q31-Ser47 2000.1 versus calculated 2001.0 Da). Phosphorylation is known to alter the stability of proteins and their resistance to proteolysis [32,33]. Our results suggest that Ser47 phosphorylation stabilizes the propeptide of PCSK9 by preventing its proteolysis. As well, cleavage of the propeptide of the R46L and E49A PCSK9 variants, but not E49D PCSK9 variant, suggests that charge distribution around this site is also important for its stability.

Example 5

PCSK9 is Phosphorylated in its C-Terminal Domain

To further examine PCSK9 phosphorylation, we grew untransfected and transfected hPCSK9(WT)-V5-expressing HepG2 cells in media containing $P^{32}$-orthophosphate, immunoprecipitated PCSK9 from cells and media, and analysed samples by SDS-PAGE fractionation followed by phospho-imaging (FIG. 6A). Lanes 1-2 and 3-4 represent immunoprecipitated PCSK9 from media and TCL of HepG2, respectively. PCSK9 and its co-immunoprecipitating propeptide were secreted as phosphoproteins whereas no phospho-PCSK9 or -prodomain were detected intracellularly. Radiolabeling and analyses were also conducted for untransfected and transfected Huh7 cells hPCSK9(WT) (lanes 6-7, respectively). Again the phosphorylated form of PCSK9 and its propeptide were only detected extracellularly (data not shown). These results, and the MS analyses presented previously, suggest that phosphorylation occurs just prior to PCSK9 secretion from the cell, or after secretion by an ectokinase [34]. Quantification of the ratio of $PO_4^{2-}$-propeptide to $PO_4^{2-}$-PCSK9 is shown below each lane. The ratio of PCSK9 propeptide to mature PCSK9 phosphorylation for endogenous protein secreted into the media from Huh7 cells was 1.9±0.1 (n=3) and 1.0±0.1 for HepG2 cells (n=3; p=0.006), reflecting the significantly higher level of phosphorylation of PCSK9 propeptide in Huh7 versus HepG2 shown earlier (FIG. 2). This difference was not due to changes in the amount of total PCSK9 relative to its propeptide as assessed by 35S-Met/Cys labeling of PCSK9 (data not shown). The minor, but specific band just above the major propeptide band represents the propeptide generated by the alternate signal peptidase cleavage following Ala28 instead of Ala30, as shown in the mass spectra previously (FIG. 2E-H and FIG. 5A-H).

Figure 6:
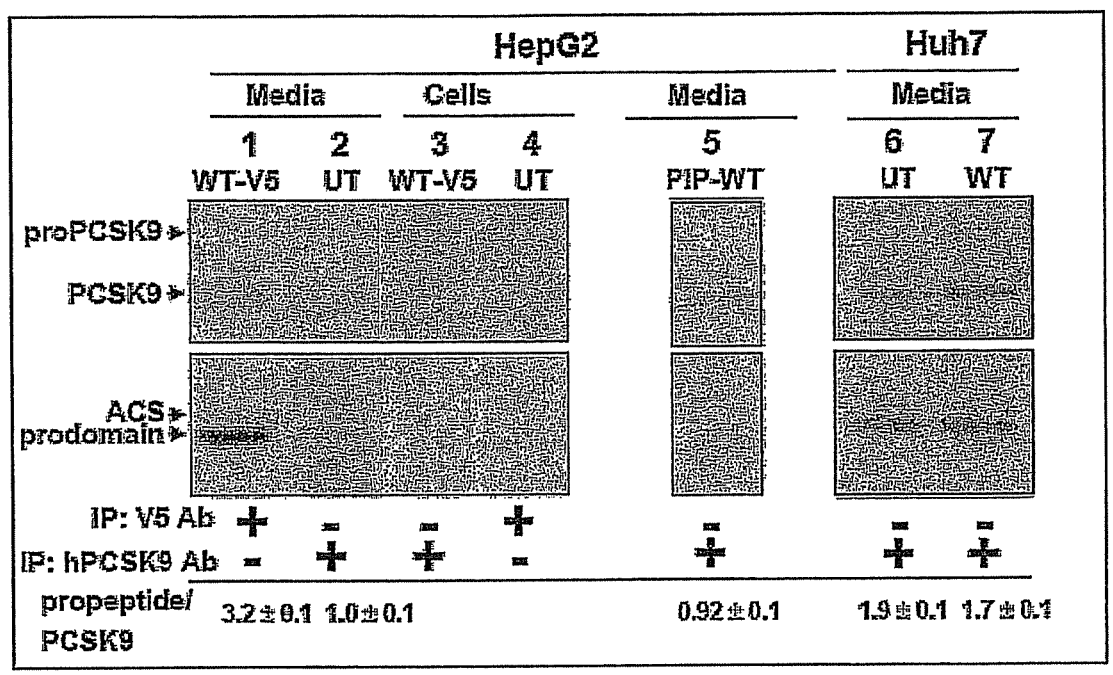
FIG. 6 shows the prodomain and mature PCSK9 are secreted as phosphoprotein in vitro. HepG2 and Huh7 cells untransfected (lanes 2, 4 and 6) and transfected expression vector for either untagged (lane 7) or V5-tagged hPCSK9 (lanes 1, 3 and 5) were radiolabeled with 32P-orthophosphate as per the Examples (see methods and materials). Total cell lysates and media were immunoprecipitated with anti-hPCSK9 Ab or anti-V5 Ab and fractionated by SDS-PAGE for phosphorimaging as per the Examples (see methods and materials). Lane 5 represents the post-immunoprecipitation of endogenously labeled protein following a primary immunoprecipitation for overexpressed V5-tagged protein. The positions of PCSK9, propeptide and alternate propeptide signal peptidase cleavage product (ACS) are noted. Quantitation of the ratio of phosphorylation for propeptide to PCSK9 is shown below each lane. Analyses were conducted on at least 3 independent experiments.

We also noted that that the ratio of $PO_4^{2-}$ propeptide/$PO_4^{2-}$ PCSK9 differed between endogenous PCSK9 (FIG. 6, lane 2; 1.0±0.1) and hPCSK9(WT)-V5 (FIG. 6, lane 1; 3.2±0.1) secreted from HepG2 cells. The attenuated phosphorylation of V5-tagged versus endogenous PCSK9 could be (1) a consequence of saturation of the responsible kinase upon overexpression or (2) the C-terminal V5-tag has affected the conformation of PCSK9 preventing kinase accessibility. To test the first possibility we carried out sequential IP of V5-tagged PCSK9 followed by endogenous PCSK9 from transfected HepG2 cells (FIG. 6A). Phosphorylation of endogenous secreted PCSK9 was identical in transfected (FIG. 6A, lane 5, 0.92±0.01, n=3) and untransfected HepG2 cells (FIG. 6, lane 2; 1.0±0.1, n=3, p=0.39) so the responsible kinase was not saturated. To examine the second possibility, transfection of untagged hPCSK9(WT) into Huh7 cells did not affect C-terminal phosphorylation (1.7±0.1, n=4; FIG. 6, lane 7) when compared to endogenous PCSK9 from the same cell line (1.9±0.1, n=3, p=0.2; FIG. 6, lane 6). The same result was noted when this experiment was duplicated in the cell line HepG2 (data not shown).

In addition, there is a commercially available antibody whose epitope (C679RSRHLAQASQELQ692) was directed toward the C-terminus of PCSK9 and contained a potential consensus site of phosphorylation [29] (SXE/S(P), in this case S688QE. This antibody reacted with immunoprecipitates of transfected V5-labeled PCSK9 (FIG. 7A, lane 1) but was unable to detect endogenous PCSK9 immunoprecipitates (FIG. 7A, lane 2). However dephosphorylation of immunoprecipitated endogenous PCSK9 with SAP, restored antibody recognition (FIG. 7A, lanes 3 and 4). Of significance, this modification also occurs at Ser 688 in vivo as assessed by immunoblotting of immunoprecipitates of PCSK9 from human plasma in the absence and presence of SAP (FIG. 7B, lanes 1 and 2, respectively). Mass spectral analyses of immunoprecipitates using preimmune sera (FIG. 7C) and immune sera PCSK9 (FIG. 7D) and human plasma shows that its propeptide also circulates as a phosphoprotein (FIG. 7D; observed mass 13919Da versus calculated 13915.5Da). FIG. 7C shows non specific peaks that are immunoprecipitated with pre-immune sera.

Example 6

Figure 8:
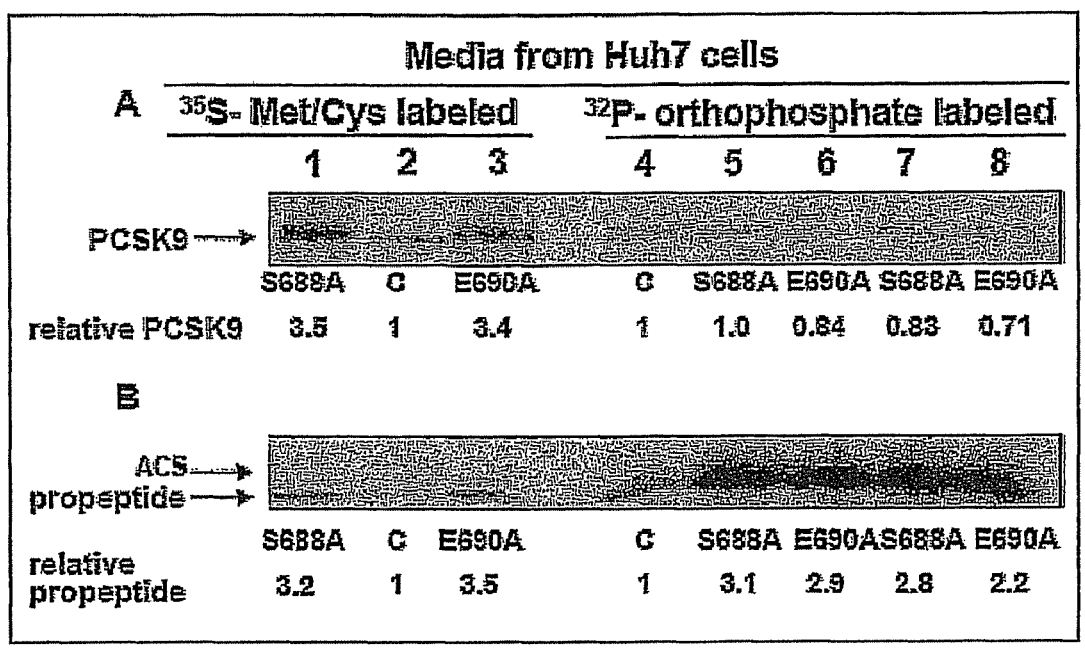
FIG. 8A-B shows site-directed mutagenesis of the C-terminal phosphorylation region of PCSK9. Huh7 cells untransfected (lanes 2 and 4) and transfected with cDNAs encoding either untagged (lane 1, 3 and 5-8) or PCSK9 C-terminal variants (as labeled) were radiolabeled with either 35S-Met/Cys (lanes 1-4) or 32P-orthophosphate (lanes 4-8) as per the Examples (see Methods and Materials). Media were immunoprecipitated with anti-hPCSK9 Ab, fractionated by SDS-PAGE for phosphoimaging as per Examples (methods and materials). The positions of PCSK9, propeptide and alternate propeptide signal peptidase cleavage product (ACS) are noted. Quantitation of the ratio of total protein immunoprecipitated (setting untransfected endogenous-C as 1) is shown below each lane.

Phosphorylation of C-Terminal PCSK9 was Also Dependent on Golgi Casein Kinase Like Activity To confirm and determine the consensus site of phosphorylation within the C-terminal of PCSK9, we cultured Huh7 cells, untransfected and transfected with expression vectors for untagged hPCSK9 mutants in media containing $^{32}$P-orthophosphate. We immunoprecipitated PCSK9 from these media, and analysed it by SDS-PAGE fractionation followed by phosphorimaging. To assess total protein expression $^{35}$S-Met/Cys labeling was carried out (FIG. 8). There was ~3.5× more expression of both the S688A (lane 1A and B; 3.5× for PCSK9, and 3.2× for its propeptide, respectively) and E690A PCSK9 mutants (lane 3A and B; 3.4× for PCSK9, and 3.5× for its propeptide, respectively) when compared to endogenous levels of PCSK9 or its propeptide (lane 2A and B; both set as 1). The mutation of either S688A (lanes 5B and 7B) or E690A (lanes 6B and 8B) in the C-terminal region of PCSK9 did not affect propeptide phosphorylation which was also ~3× more than endogenous PCSK9 (lane 4B). However, mutation of either S688A (lanes 5A and 7A) or E690A (lanes 6A and 8A) prevented phosphorylation at the C-terminus of PCSK9 since only background levels of phosphorylation due to endogenous PCSK9 was measured (lane 4A). This can also be seen by comparing the ratio of propeptide/PCSK9 phosphorylation for wildtype untagged PCSK9 (1.9; FIG. 6, lane 6) with both of these untagged mutants (FIG. 8, lanes 5-8). The requirement of an E at n+2 suggests that, like for propeptide phosphorylation, this phosphorylation is carried out by a GCK-like kinase [consensus site SXE/S(p)].

PCSK9 undergoes several post-translational modifications: while in the ER it is glycosylated at a single N-linked site at amino acid 533 (NCS) that is further matured in the golgi increasing the molecular mass of secreted versus intracellular PCSK9 by ~2200 Da [4]. We have also reported the sulfation of Tyr38 within the propeptide of PCSK9. Sulfation occurred just prior to secretion from the trans-golgi network since it was barely detected intracellularly [4, 5]. In this study, we report that secreted PCSK9 is phosphorylated at Ser47 in its propeptide and at Ser688 in its CHRD. Phosphorylation of the propeptide was cell-type specific with 70±4% phosphorylation in HuH7 cells, followed by 54±2% in HepG2 cells, 23±0.2% in Hek293 cells and none in CHOK1 cells (FIG. 2). It also occurred very late in the secretory pathway or at the cell surface since no phosphorylated PCSK9 was detected intracellularly by either MS analyses of immunoprecipitates or radiolabeling followed by immunoprecipitation and autoradiography; two very sensitive techniques.

Figure 9:
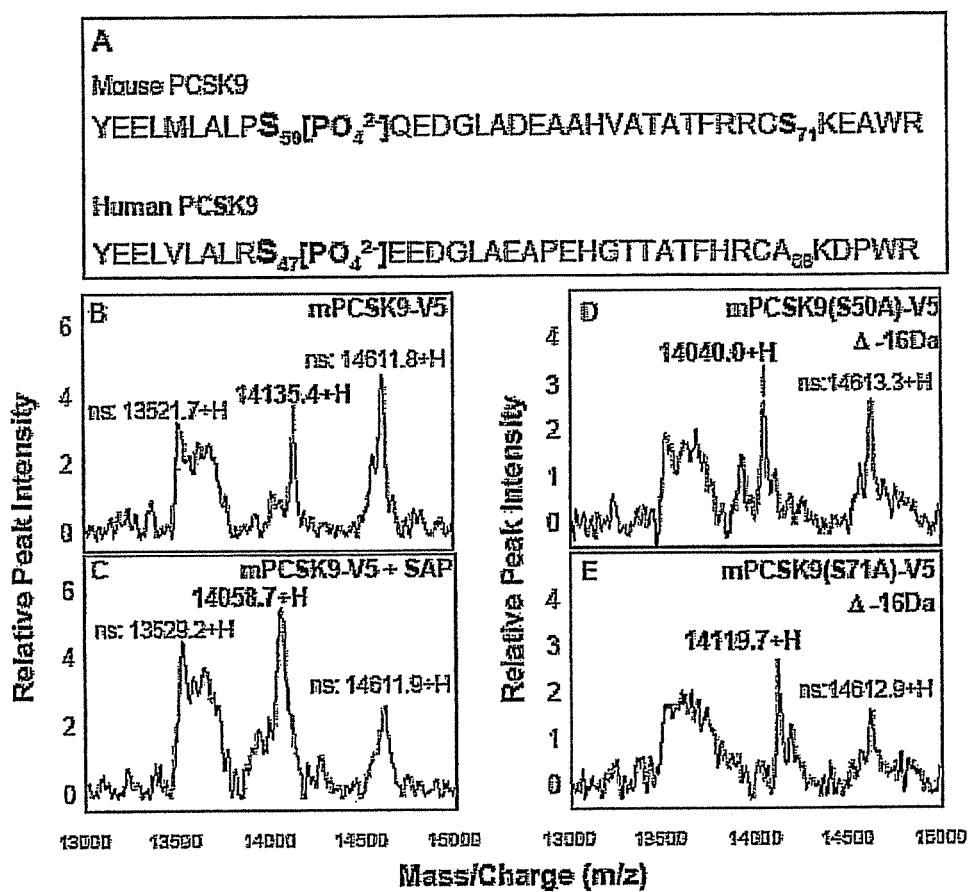
FIG. 9A-E shows the alignment of the amino acid sequence of the propeptide of mouse and human PCSK9 and encompasses two possible sites of serine phosphorylation in the mouse (in bold). Panels B and C represent time-of-flight mass spectral analyses (TOF-MS) of the molecular forms of V5-tagged overexpressed mouse PCSK9 propeptide immunoprecipitated from the media of Huh7 cells with anti-V5 antibody in the absence of (B) and presence (C) of SAP. Panels D and E represent TOF-MS analyses of the propeptide of V5-tagged PCSK9 variants as labeled from the media of transfected and overexpressing Huh7 cells. For each variant the change in molecular mass due to the specific amino acid change is shown as ΔDa.

Serine phosphorylation occurred within the site RS47EED and was 100% dependant on Glu at the n+2 position (FIG. 2). This site is completely conserved among primates except for the Tamarin monkey where an amino acid change occurs at n+3 (D50E) which should not affect propeptide phosphorylation based on our site-directed mutagenesis results (FIG. 5). There are two possible sites of prodomain phosphorylation in the mouse and rat. The first site is conserved between human (RSEED), mouse and rat PCSK9 (both PSQED; FIG. 9). Although, the n−1 and n+1 residues differ, they still conform to a consensus phosphorylation site for GCK (SXE). The second site is only conserved between mouse and rat (CSKEA), not human (CAKEP; FIG. 9). The prodomain of mouse PCSK9 is phosphorylated (FIG. 9B-C) at PS50QED (FIG. 9D) and not at CAKEP (FIG. 9E)

Phosphorylation is an important post translational modification shown to affect several parameters including; (1) stability and turnover by interfering with or promoting proteolysis [32, 33], (2) activating or inactivating enzymes [35], (3) affect sub-cellular localization and transport [36, 37] and (4) affecting protein-protein interactions and/or protein conformation[33, 38, 39]. Biophysical studies of the structure of PCSK9 have shown that its propeptide region is solvent exposed, and crystal structure studies of PCSK9 have failed in this region due to lack of electron density [15, 19, 40, 41] and therefore descriptions of the prodomain of PCSK9 begin downstream of the site of phosphorylation (Ser47) at Thr61 [15, 19]. Neither study predicts direct interaction of the PCSK9 propeptide with the LDLR EGF-A domain; however, it is interesting to note that several documented 'loss of function' PCSK9 variants such as the R46L [31, 42, 43] occur within this domain, suggesting a regulatory function for this region. We provide evidence here that phosphorylation at Ser47, as well as charge distribution within this propeptide region, stabilizes it against proteolysis following this site of post translational modification (FIG. 5). Recently, Kwon and colleagues [19] reported that recombinant propeptide D53-PCSK9 exhibited greater than 7-fold affinity for the extracellular EGF-A domain of LDLR in comparison to wild type PCSK9, supporting the results herein that the N-terminal region of the propeptide of PCSK9 may modulate or stabilize its interaction with LDLR, either directly or indirectly.

Figure 7:
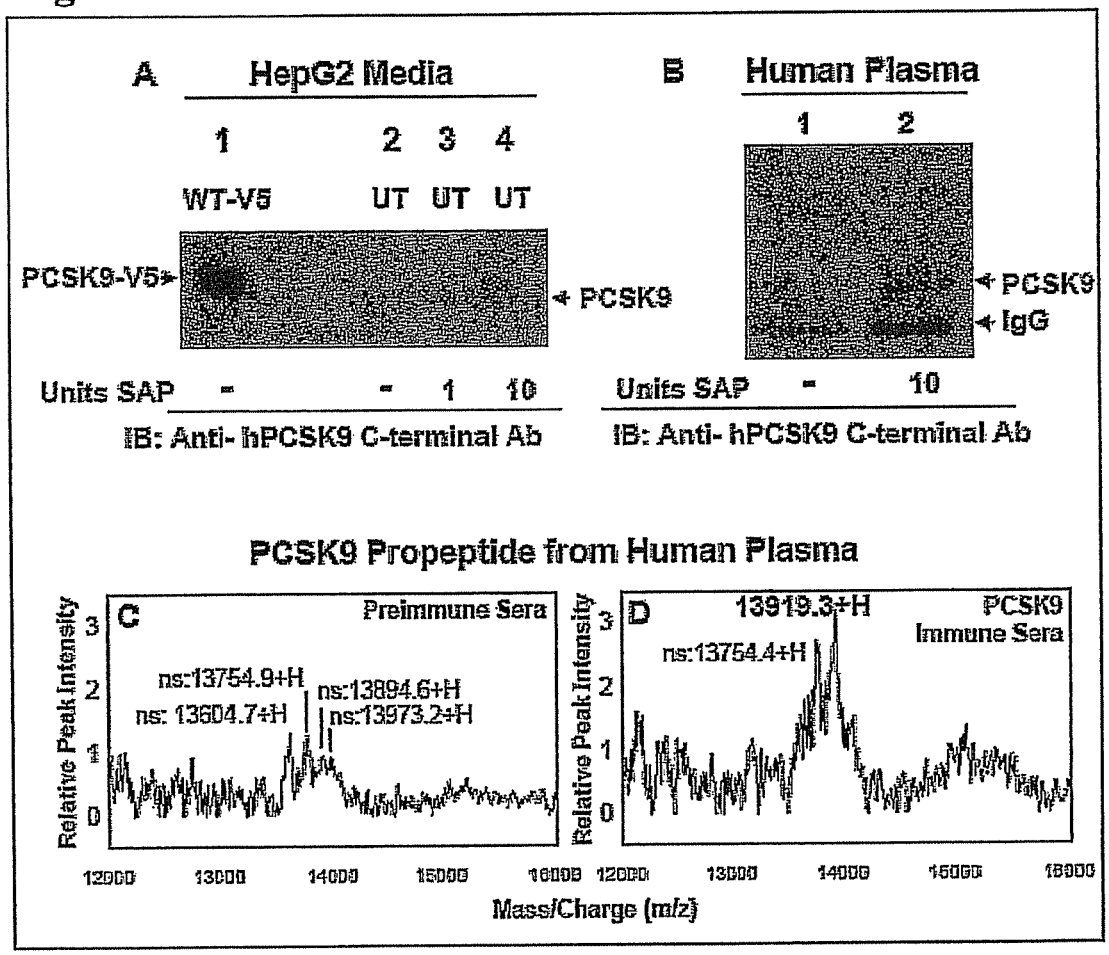
FIG. 7A-D shows the prodomain and mature PCSK9 are secreted as phosphoproteins in vivo. Panel A represents the immunoprecipitation of overexpressed V5-labelled PCSK9 (lane 1) or endogenous PCSK9 (lanes 2-4) from the media of HepG2 cells followed by dephosphorylation of immunoprecipitates (lane 3 and 4) and immunoblotting analyses with the anti-hPCSK9 C-terminal Ab (Imgenex). Panel B represents the immunoprecipitation of PCSK9 from human plasma with the anti-hPCSK9 Ab followed by incubation in the absence (lane 1) or presence (lane 2) of shrimp alkaline phosphatase and immunoblotting analyses with the anti-hPCSK9 C-terminal Ab (Imgenex). IgG; immunoglobulin band. Panel C and D represent time-of-flight mass spectral analyses (TOF-MS) of the molecular forms of PCSK9 propeptide immunoprecipitated from human plasma with either preimmune sera (C) or immune (anti-hPCSK9 Ab; D). ns: non-specific peaks.

We also report that PCSK9 is phosphorylated in its CHRD, five amino acids from its C-terminus at Ser688, within the sequence QAS688QELQ (FIGS. 6 and 7). Like the N-terminal propeptide region of PCSK9, its C-terminal region (from amino acids 683-692) has not been characterized by existing crystal structure studies [15], and while this site is not conserved in the mouse or rat (KASWVQ and KASWVHQ, respectively), it is 100% conserved among 12 of the 14 primate species [44].

We also demonstrated that the addition of the C-terminal V5-tag greatly diminished phosphorylation at Ser688 (FIG.

6). Many binding, co-localization and crystal structure studies for PCSK9 and LDLR have been carried out using tagged and therefore hypo-phosphorylated PCSK9 and/or employing cell lines in which propeptide phosphorylation is diminished or absent (that is, the HEK293 and CHO cell lines, respectively, FIG. 2).

Example 7

Overexpression of Engineered, Unphosphorylated PCSK9 Variants Leads to Decrease LDLR Degradation in Cultures of Liver Cells PCSK9 phosphorylation mutants and their activity against the LDLR receptor is shown in FIG. 10. Huh7 cells were untransfected (C-control) or transiently transfected with cDNAs encoding either wild-type (WT) PCSK9, or the naturally-occurring propeptide mutants shown to decrease PCSK9 phosphorylation; A53V PCSK9 and R46L PCSK9 or the engineered propeptide mutants that prevent phosphorylation; S47A PCSK9, E49A PCAK9 and E49D PCSK9 or the engineered C-terminal mutants that prevent phosphorylation; S688A and E690A. 72 hours post-transfection spent media and total cell lysates were collected as described herein. 50 µg of total cell lysates were fractionated through a 7% NuPAGE Tris-Acetate Gel (Invitrogen) and immunoblotted for LDLR as described below. The protein signals were quantified by densitometry using Syngene Chemigenius 2XE imager and Gene Tools software. All values were made relative to values from control cells set as 1 and presented as mean±SEM (n=3). Data were analyzed using GraphPad Prism 5.0 statistical software with significance defined as p<0.05.

Figure 10A:
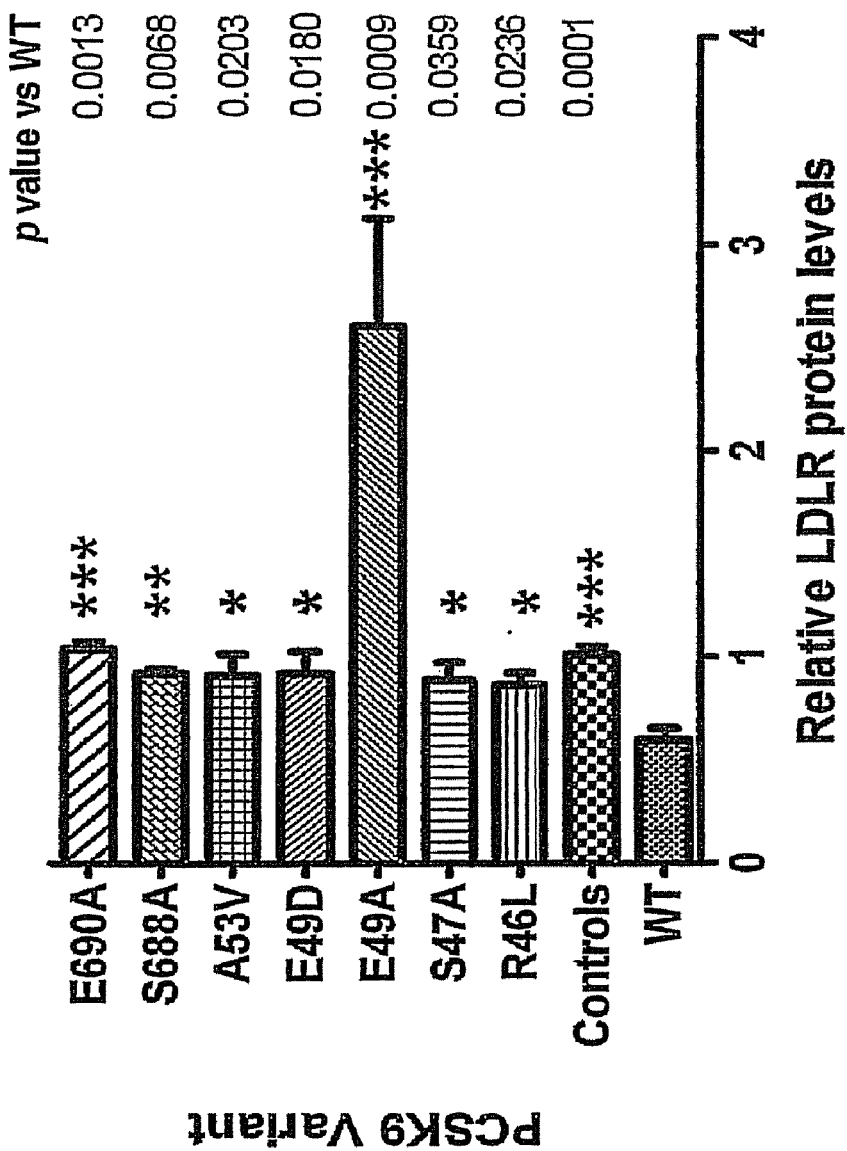
FIG. 10A,B shows results for PCSK9 phosphorylation mutants and their activity against the LDLR. Huh7 cells were untransfected (C-control) or transiently transfected with cDNAs encoding either wild-type (WT) PCSK9, or the naturally-occurring propeptide mutants shown to decrease PCSK9 phosphorylation; A53V PCSK9 and R46L PCSK9 or the engineered propeptide mutants that prevent phosphorylation; S47A PCSK9, E49A PCAK9 and E49D PCSK9, the engineered C-terminal mutants that prevent phosphorylation; S688A and E690A or the engineered propeptide mutants that mimic PCSK9 propeptide phosphorylation; S47E PCSK9.
Figure 10B:
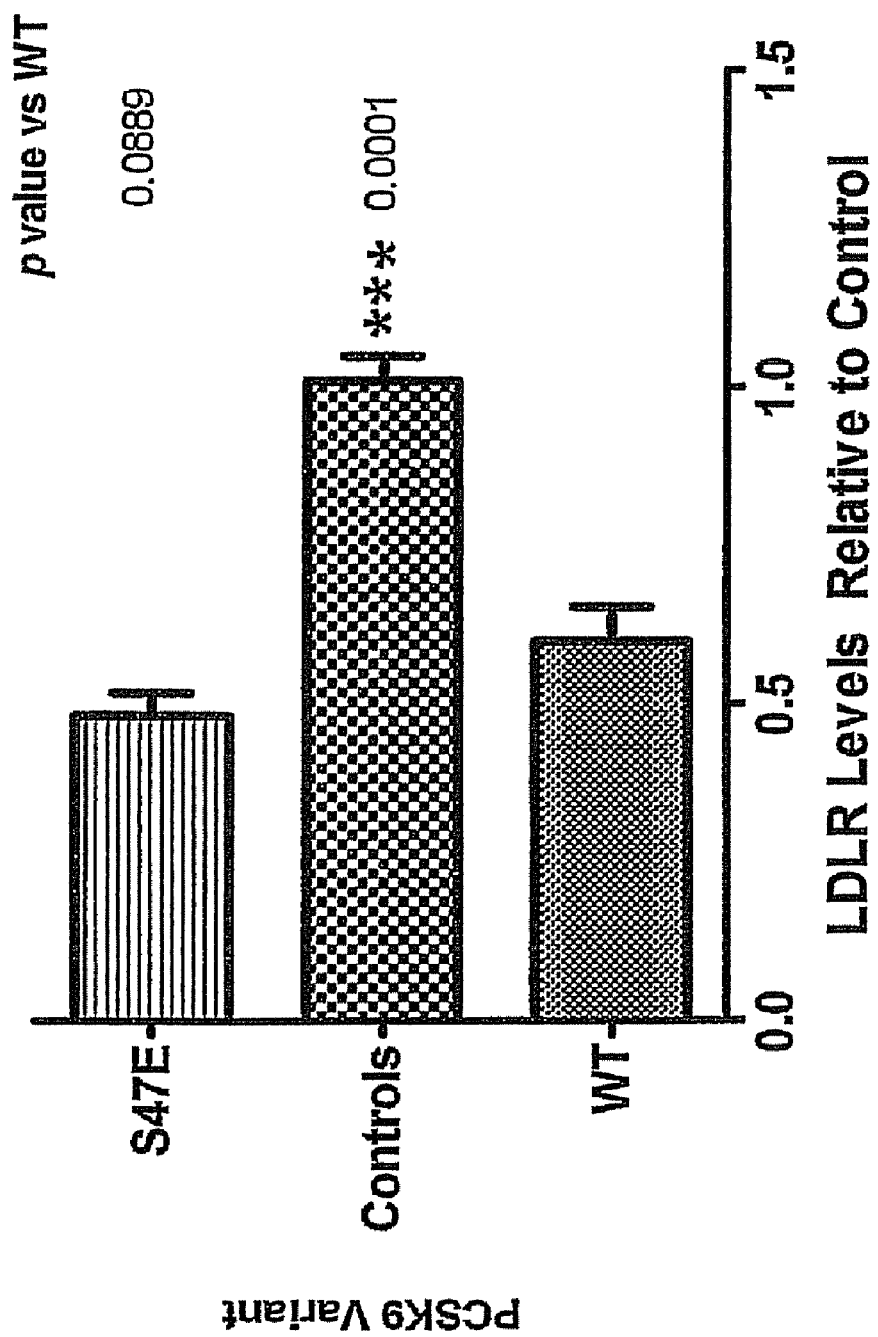

The results suggest that preventing phosphorylation of either the propeptide or C-terminal of PCSK9 decreases its activity toward LDLR since the level of LDLR increased significantly in comparison to cells transfected with wildtype phosphorylated PCSK9 (see FIG. 10A). Conversely, overexpression of a PCSK9 variant that mimics phosphorylation of the prodomain S47 (S47E) leads to increased LDLR degradation in cultures of liver cells (see FIG. 10B).

Example 8

Inhibition of PCSK9 Phosphorylation by a Kinase Inhibitor Leads to an Increase in LDLR Levels The level of LDLR was quantified in Huh7 cells by immunoblotting of total cell lysates (50 µg) in response to overnight incubation without (control) or with two different kinase inhibitors, staurosporine (SSP at 200 nm) or GK (genistein at 25 µg/ml) (FIG. 11A). Huh7 cells were seeded onto 6 well plates and grown to 80% confluency in DMEM (Dulbecco's Modified Eagle's Medium)+10% (v/v) FBS (fetal bovine serum)+280 µg/ml GTM (gentamycin). Cells were then incubated for 16 hrs in the same media in the presence or absence of kinase inhibitor; staurosporine (SSP at 200 nm) or GK (genistein at 25 µg/ml). Cells were lysed in 1XRIPA buffer [50 mM Tris (pH 7.6), 150 mM NaCl, 1% (v/v) NP-40, 0.5% (w/v) DOC, 0.1% (w/v) SDS] in the presence of inhibitors, as above. Lysates were rotated at 4° C. for 30 min, centrifuged at 13,000×g for 3 min and supernatants collected. Protein concentrations in total cell lysates were determined by the Bradford dye-binding method using Bio-Rad's Protein Assay Kit (Bio-Rad; Mississauga, ON, CAN). LDLR levels were analyzed by immunoblotting following a standard protocol. The protein signals were quantified by densitometry using Syngene Chemigenius 2XE imager and Gene Tools software.

Prior to radiolabeling cells were incubated for 4 hours in serum-free DMEM without sodium phosphate (Invitrogen) or methionine/cysteine (Met/Cys) free DMEM (Invitrogen) with or without kinase inhibitor, as indicated, and then incubated for 16 hrs in the same media in the presence of either 250 µCi 32P-orthophosphate or 250 µCi $^{35}$S-Met/Cys with or without kinase inhibitor, as indicated (S35 data not shown). Spent media was harvested and immunoprecipitated for PCSK9 as described below. Samples were fractionated through a 12% SDS-PAGE. Following electrophoresis gels were dried and visualized by phosphorimaging using a Typhoon Imager. All values were made relative to values from untreated cells set as 1.

FIG. 11A clearly shows that that incubation of Huh7 cells in the presence of SSP that prevented PCSK9 phosphorylation (but not GK) also resulted in increased levels of LDLR. FIG. 11B Lane C-shows the level of phosphorylation of PCSK9 and its prodomain under normal conditions. When cells are incubated in presence of stauroporine (SSP) neither PCSK9 nor its prodomain are phosphorylated. But under the same conditions genestein (GK; a protein tyrosine kinase inhibitor) does not affect PCSK9 phosphorylation. It remains at about the level of PCSK9 from untreated control (C) cells. Protein levels are not affected by these inhibitors as assessed by S35 labelling (not shown).

Based on the results demonstrated in FIG. 11, it is shown that administration of an inhibitor of PCSK9 phosphorylation can be used to prevent PCSK9 phosphorylation and that such a prevention increases LDLR protein levels. Accordingly there is provided a method of increasing LDLR levels comprising administering a serine kinase inhibitor to a cell, cell culture or subject to increase LDLR levels. In a preferred embodiment, the serine kinase inhibitor is a broad spectrum serine kinase inhibitor, for example, but not limited to staurosporine.

Example 9

Addition of Peptides Directed Against PCSK9 Sites of Phosphorylation can Protect Against LDLR Degradation and are Potential Therapeutic Targets to Decrease LDLC by Increasing LDLR Levels in Cells Cells were seeded onto 6 well plates and grown to ~80% confluency. All cell lines were grown in DMEM (Dulbecco's Modified Eagle's Medium)+10% (v/v) FBS (fetal bovine serum)+280 µg/ml GTM (gentamycin). In this case, cells were incubated overnight in the same media in the absence of FBS for 12 hours. Peptides are then added to media minus FBS, and at indicated concentrations and this media+peptide is added onto cells cultured for additional 24 hours. Following this incubation we collected the spent media and total cell lysates (TCL) in the presence of protease inhibitor cocktail. 50 µg of proteins from TCL were then fractionated by SDS-PAGE, transferred to nitrocellulose and immunoblotted following standard protocols with a commercial anti LDLR antibody. The protein signals for LDLR were quantified by densitometry using Syngene Chemigenius 2XE imager and Gene Tools software. All values are made relative to values from untreated control cells set as 1 and presented as mean±SEM (n<3).

Figure 12A:
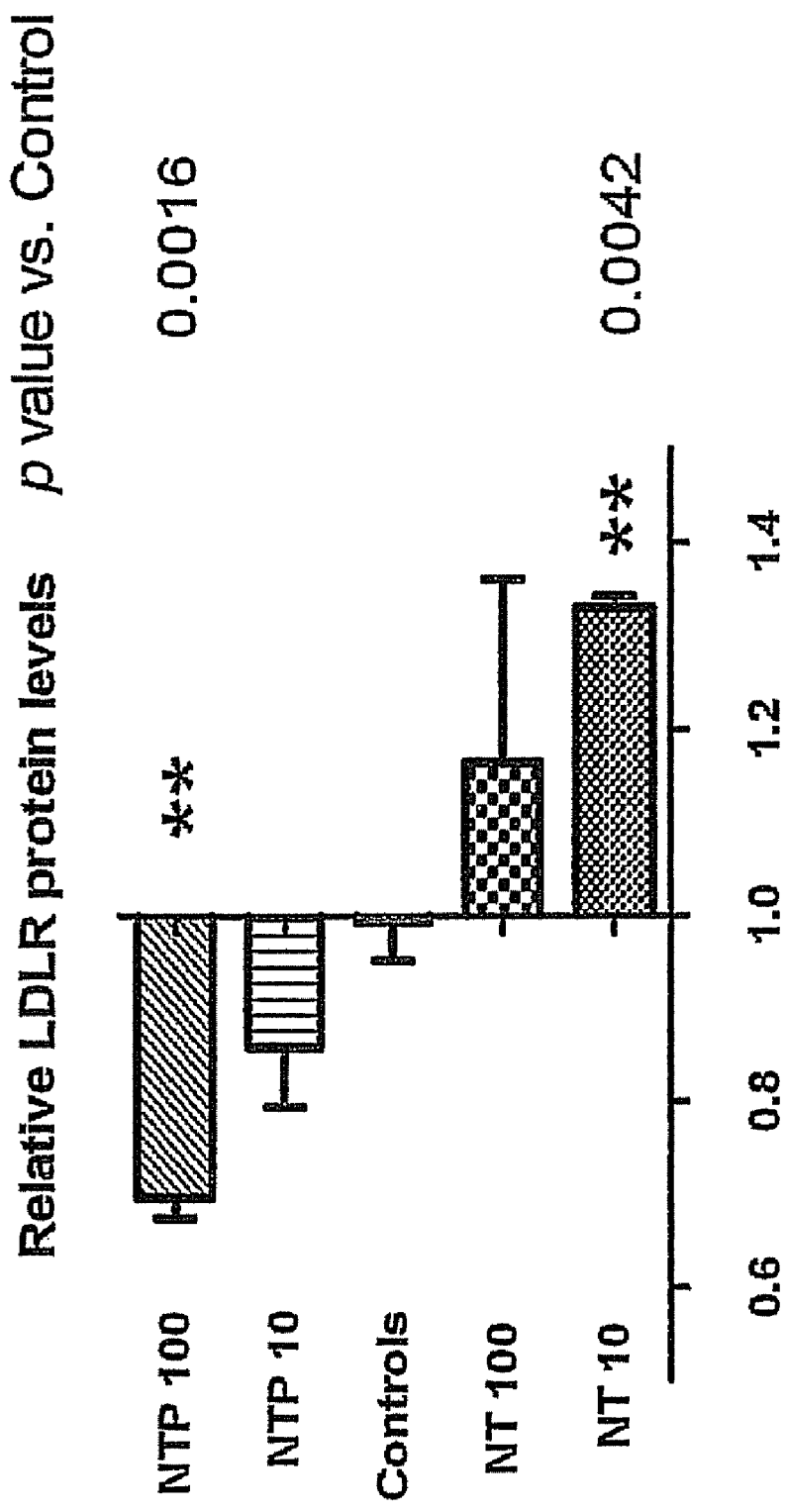
FIG. 12A,B shows results that indicate addition of peptides directed against PCSK9 sites of phosphorylation can protect against LDLR degradation and are potential therapeutic targets to decrease LDLC by increasing LDLR levels in Huh7 cells.
Figure 12B:
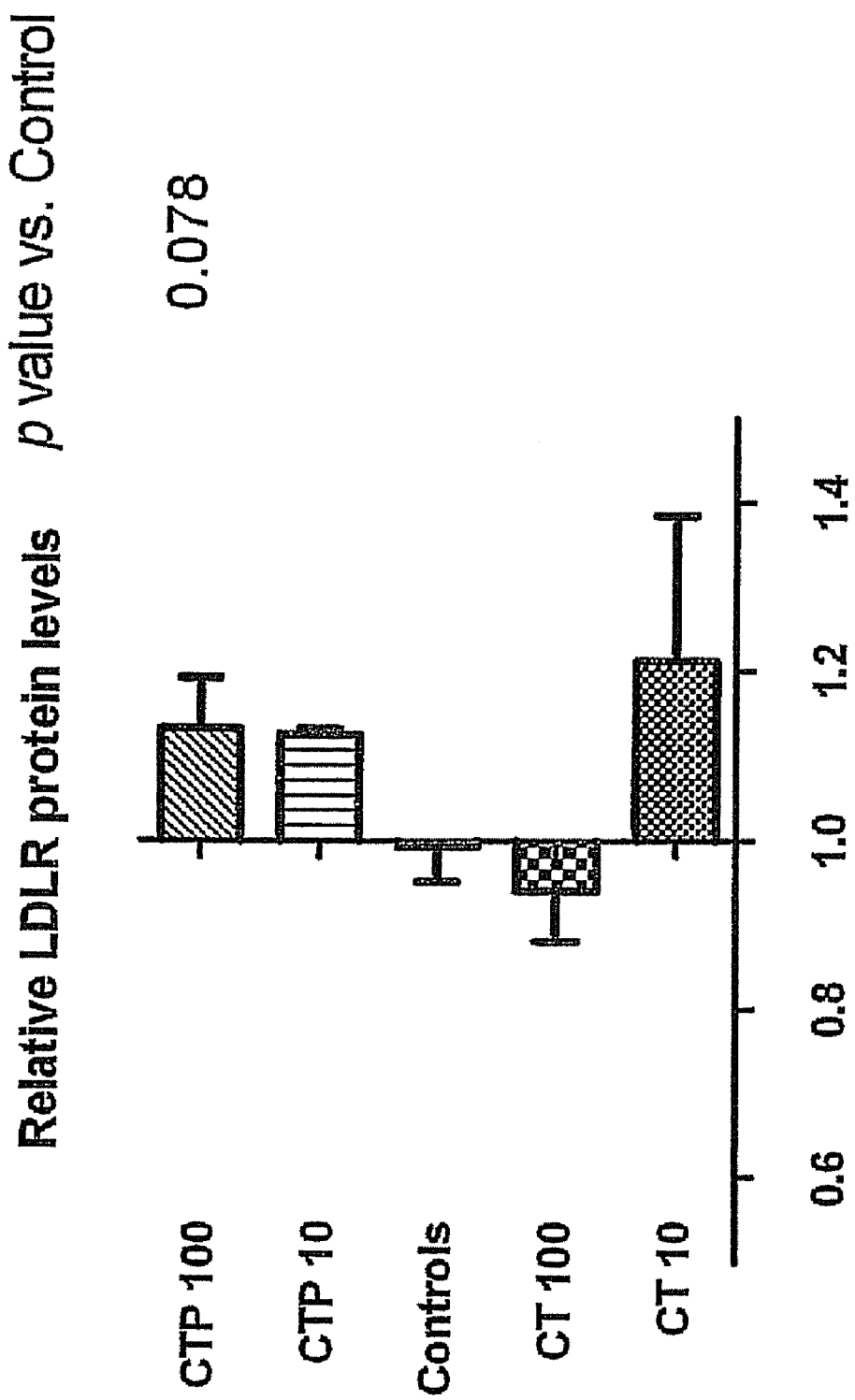

The results shown in FIG. 12A,B suggest that addition of unphosphorylated PCSK9 polypeptide or polypeptide fragment, for example, but not limited to SEQ ID NO:2 comprising Serine 47 at both 10 and 100 µM protect LDLR from degradation in comparison to control while addition of phosphorylated peptides, for example, but not limited to SEQ ID NO:3 comprising phosphoSerine (at both 10 and 100 μM) accentuate LDLR degradation. Addition of unphosphorylated PCSK polypeptide or polypeptide fragment, for example, but not limited to SEQ ID NO:4 comprising Serine 688 at 10 μM or phosphorylated polypeptide fragment, for example but not limited to SEQ ID NO:5 comprising phosphoSerine 688 at 10 or 100 μM protect LDLR from degradation in comparison to control. Accordingly, there is provided a method of modulating LDLR degradation comprising administering a PCSK9 polypeptide or polypeptide fragment to a cell, cell culture or subject to affect LDLR degradation. Further, there is provided a method of protecting LDLR from degradation comprising administering an unphosphorylated PCSK9 polypeptide or polypeptide fragment of SEQ ID NO:1 that comprises Serine 47, a phosphorylated PCSK9 polypeptide or polypeptide fragment, for example, but not limited to SEQ ID NO:1 that comprises a phosphorylated or unphosphorylated Serine 688 to a cell, cell culture or subject to protect LDLR degradation. In still a further embodiment, there is provided a method of accentuating LDLR degradation comprising administering a phosphorylated PCSK9 polypeptide or polypeptide fragment of SEQ ID NO:1 that comprises phosphoSerine 47. Other methods as defined above are also contemplated by the present invention.

The present invention has been described with regard to one or more embodiments. However, it will be apparent to persons skilled in the art that a number of variations and modifications can be made without departing from the scope of the invention as defined in the claims.

The contents of all references and patents cited throughout this application are hereby incorporated by reference in their entirety.

REFERENCES

1. Seidah N G, Khatib A M & Prat A (2006) The proprotein convertases and their implication in sterol and/or lipid metabolism. Biol Chem 387, 871-877.
2. Seidah N G, Benjannet S, Wickham L, Marcinkiewicz J, Jasmin S B, Stifani S, Basak A, Prat A & Chretien M (2003) The secretory proprotein convertase neural apoptosis-regulated convertase 1 (NARC-1): liver regeneration and neuronal differentiation. Proc Natl Acad Sci USA 100, 928-933.
3. Seidah N G & Prat A (2002) Precursor convertases in the secretory pathway, cytosol and extracellular milieu. Essays Biochem 38, 79-94.
4. Benjannet S, Rhainds D, Essalmani R, Mayne J, Wickham L, Jin W, Asselin M C, Hamelin J, Varret M, Allard D, Trillard M, Abifadel M, Tebon A, Attie A D, Rader D J, Boileau C, Brissette L, Chretien M, Prat A & Seidah N G (2004) NARC-1/PCSK9 and its natural mutants: zymogen cleavage and effects on the low density lipoprotein (LDL) receptor and LDL cholesterol. J Biol Chem 279, 48865-48875.
5. Benjannet S, Rhainds D, Hamelin J, Nassoury N & Seidah N G (2006) The Proprotein Convertase (PC)PCSK9 Is Inactivated by Furin and/or PC5/6A: FUNCTIONAL CONSEQUENCES OF NATURAL MUTATIONS AND POST-TRANSLATIONAL MODIFICATIONS. J Biol Chem 281, 30561-30572.
6. Lagace T A, Curtis D E, Garuti R, McNutt M C, Park S W, Prather H B, Anderson N N, Ho Y K, Hammer R E & Horton J D (2006) Secreted PCSK9 decreases the number of LDL receptors in hepatocytes and in livers of parabiotic mice. J Clin Invest 116, 2995-3005.
7. Zhao Z, Tuakli-Wosomu Y, Lagace T A, Kinch L, Grishin N V, Horton J D, Cohen J C & Hobbs H H (2006) Molecular characterization of loss-of-function mutations in PCSK9 and identification of a compound heterozygote. Am J Hum Genet. 79, 514-523.
8. Rashid S, Curtis D E, Garuti R, Anderson N N, Bashmakov Y, Ho Y K, Hammer R E, Moon Y A & Horton J D (2005) Decreased plasma cholesterol and hypersensitivity to statins in mice lacking Pcsk9. Proc Natl Acad Sci USA 102, 5374-5379.
9. Maxwell K N & Breslow J L (2004) Adenoviral-mediated expression of Pcsk9 in mice results in a low-density lipoprotein receptor knockout phenotype. Proc Natl Acad Sci USA 101, 7100-7105.
10. Maxwell K N, Fisher E A & Breslow J L (2005) Overexpression of PCSK9 accelerates the degradation of the LDLR in a post-endoplasmic reticulum compartment. Proc Natl Acad Sci USA 102, 2069-2074.
11. Lambert G (2007) Unravelling the functional significance of PCSK9. Curr Opin Lipidol 18, 304-309.
12. Zhang D W, Lagace T A, Garuti R, Zhao Z, McDonald M, Horton J D, Cohen J C & Hobbs H H (2007) Binding of proprotein convertase subtilisin/kexin type 9 to epidermal growth factor-like repeat A of low density lipoprotein receptor decreases receptor recycling and increases degradation. J Biol Chem 282, 18602-18612.
13. Qian Y W, Schmidt R J, Zhang Y, Chu S, Lin A, Wang H, Wang X, Beyer T P, Bensch W R, Li W, Ehsani M E, Lu D, Konrad R J, Eacho P I, Moller D E, Karathanasis S K & Cao G (2007) Secreted PCSK9 downregulates low density lipoprotein receptor through receptor-mediated endocytosis. J Lipid Res 48, 1488-1498.
14. Nassoury N, Blasiole D A, Tebon Oler A, Benjannet S, Hamelin J, Poupon V, McPherson P S, Attie A D, Prat A & Seidah N G (2007) The cellular trafficking of the secretory proprotein convertase PCSK9 and its dependence on the LDLR. Traffic 8, 718-732.
15. Cunningham D, Danley D E, Geoghegan K F, Griffor M C, Hawkins J L, Subashi T A, Varghese A H, Ammirati M J, Culp J S, Hoth L R, Mansour M N, McGrath K M, Seddon A P, Shenolikar S, Stutzman-Engwall K J, Warren L C, Xia D & Qiu X (2007) Structural and biophysical studies of PCSK9 and its mutants linked to familial hypercholesterolemia. Nat Struct Mol Biol 14, 413-419.
16. Naoumova R P, Tosi I, Patel D, Neuwirth C, Horswell S D, Marais A D, van Heyningen C & Soutar A K (2005) Severe hypercholesterolemia in four British families with the D374Y mutation in the PCSK9 gene: long-term follow-up and treatment response. Arterioscler Thromb Vasc Biol 25, 2654-2660.
17. Timms K M, Wagner S, Samuels M E, Forbey K, Goldfine H, Jammulapati S, Skolnick M E, Hopkins P N, Hunt S C & Shattuck D M (2004) A mutation in PCSK9 causing autosomal-dominant hypercholesterolemia in a Utah pedigree. Hum Genet. 114, 349-353.
18. Fisher T S, Lo Surdo P, Pandit S, Mattu M, Santoro J C, Wisniewski D, Cummings R T, Calzetta A, Cubbon R M, Fischer P A, Tarachandani A, De Francesco R, Wright S D, Sparrow C P, Carfi A & Sitlani A (2007) Effects of pH and low density lipoprotein (LDL) on PCSK9-dependent LDL receptor regulation. J Biol Chem 282, 20502-20512.

19. Kwon H J, Lagace T A, McNutt M C, Horton J D & Deisenhofer J (2008) Molecular basis for LDL receptor recognition by PCSK9. Proc Natl Acad Sci USA 105, 1820-1825.
20. Cohen J C, Boerwinkle E, Mosley T H, Jr. & Hobbs H H (2006) Sequence variations in PCSK9, low LDL, and protection against coronary heart disease. N Engl J Med 354, 1264-1272.
21. Scartezini M, Hubbart C, Whittall R A, Cooper J A, Neil A H & Humphries S E (2007) The PCSK9 gene R46L variant is associated with lower plasma lipid levels and cardiovascular risk in healthy U.K. men. Clin Sci (Lond) 113, 435-441.
22. Mayne J, Raymond A, Chaplin A, Cousins M, Kaefer N, Gyamera-Acheampong C, Seidah N G, Mbikay M, Chretien M & Ooi T C (2007) Plasma PCSK9 levels correlate with cholesterol in men but not in women. Biochem Biophys Res Commun 361, 451-456.
23. Hooper A J, Marais A D, Tanyanyiwa D M & Burnett J R (2006) The C679X mutation in PCSK9 is present and lowers blood cholesterol in a Southern African population. Atherosclerosis.
24. Careskey H E, Davis R A, Alborn W E, Troutt J S, Cao G & Konrad R J (2008) Atorvastatin increases human serum levels of proprotein convertase subtilisin/kexin type 9. J Lipid Res 49, 394-398.
25. Price P A, Rice J S & Williamson M K (1994) Conserved phosphorylation of serines in the Ser-X-Glu/Ser(P) sequences of the vitamin K-dependent matrix Gla protein from shark, lamb, rat, cow, and human. Protein Sci 3, 822-830.
26. Horner V M, Marais A D, Charlton F, Laurie A D, Hurndell N, Scott R, Mangili F, Sullivan D R, Barter P J, Rye K A, George P M & Lambert G (2008) Identification and characterization of two non-secreted PCSK9 mutants associated with familial hypercholesterolemia in cohorts from New Zealand and South Africa. Atherosclerosis 196, 659-666.
27. Graham M E, Kilby D M, Firth S M, Robinson P J & Baxter R C (2007) The in vivo phosphorylation and glycosylation of human insulin-like growth factor binding protein-5. Mol Cell Proteomics.
28. Craig A G, Hoeger C A, Miller C L, Goedken T, Rivier J E & Fischer W H (1994) Monitoring protein kinase and phosphatase reactions with matrix-assisted laser desorption/ionization mass spectrometry and capillary zone electrophoresis: comparison of the detection efficiency of peptide-phosphopeptide mixtures. Biol Mass Spectrom 23, 519-528.
29. Tibaldi E, Arrigoni G, Brunati A M, James P & Pinna L A (2006) Analysis of a sub-proteome which co-purifies with and is phosphorylated by the Golgi casein kinase. Cell Mol Life Sci 63, 378-389.
30. Christensen B, Nielsen M S, Haselmann K F, Petersen T E & Sorensen E S (2005) Post-translationally modified residues of native human osteopontin are located in clusters: identification of 36 phosphorylation and five O-glycosylation sites and their biological implications. Biochem J 390, 285-292.
31. Kotowski I K, Pertsemlidis A, Luke A, Cooper R S, Vega G L, Cohen J C & Hobbs H H (2006) A spectrum of PCSK9 alleles contributes to plasma levels of low-density lipoprotein cholesterol. Am J Hum Genet. 78, 410-422.
32. Coverley J A, Martin J L & Baxter R C (2000) The effect of phosphorylation by casein kinase 2 on the activity of insulin-like growth factor-binding protein-3. Endocrinology 141, 564-570.
33. Huber S C & Hardin S C (2004) Numerous posttranslational modifications provide opportunities for the intricate regulation of metabolic enzymes at multiple levels. Curr Opin Plant Biol 7, 318-322.
34. Jellinek D A, Chang A C, Larsen M R, Wang X, Robinson P J & Reddel R R (2000) Stanniocalcin 1 and 2 are secreted as phosphoproteins from human fibrosarcoma cells. Biochem J 350 Pt 2, 453-461.
35. Hefner Y, Borsch-Haubold A G, Murakami M, Wilde J I, Pasquet S, Schieltz D, Ghomashchi F, Yates J R, 3rd, Armstrong C G, Paterson A, Cohen P, Fukunaga R, Hunter T, Kudo I, Watson S P & Gelb M H (2000) Serine 727 phosphorylation and activation of cytosolic phospholipase A2 by MNK1-related protein kinases. J Biol Chem 275, 37542-37551.
36. Kohlstedt K, Shoghi F, Muller-Esterl W, Busse R & Fleming 1 (2002) CK2 phosphorylates the angiotensin-converting enzyme and regulates its retention in the endothelial cell plasma membrane. Circ Res 91, 749-756.
37. Jones B G, Thomas L, Molloy S S, Thulin C D, Fry M D, Walsh K A & Thomas G (1995) Intracellular trafficking of furin is modulated by the phosphorylation state of a casein kinase II site in its cytoplasmic tail. Embo J 14, 5869-5883.
38. Jones J I, D'Ercole A J, Camacho-Hubner C & Clemmons D R (1991) Phosphorylation of insulin-like growth factor (IGF)-binding protein 1 in cell culture and in vivo: effects on affinity for IGF-I. Proc Natl Acad Sci USA 88, 7481-7485.
39. Quirk P G, Patchell V B, Colyer J, Drago G A & Gao Y (1996) Conformational effects of serine phosphorylation in phospholamban peptides. Eur J Biochem 236, 85-91.
40. Hampton E N, Knuth M W, Li J, Harris J L, Lesley S A & Spraggon G (2007) The self-inhibited structure of full-length PCSK9 at 1.9 A reveals structural homology with resistin within the C-terminal domain. Proc Natl Acad Sci USA 104, 14604-14609.
41. Piper D E, Jackson S, Liu Q, Romanow W G, Shetterly S, Thibault S T, Shan B & Walker N P (2007) The crystal structure of PCSK9: a regulator of plasma LDL-cholesterol. Structure 15, 545-552.
42. Berge K E, Ose L & Leren T P (2006) Missense mutations in the PCSK9 gene are associated with hypocholesterolemia and possibly increased response to statin therapy. Arterioscler Thromb Vasc Biol 26, 1094-1100.
43. Fasano T, Cefalu A B, Di Leo E, Noto D, Pollaccia D, Bocchi L, Valenti V, Bonardi R, Guardamagna O, Avema M & Tarugi P (2007) A novel loss of function mutation of PCSK9 gene in white subjects with low-plasma low-density lipoprotein cholesterol. Arterioscler Thromb Vasc Biol 27, 677-681.
44. Ding K, McDonough S J & Kullo I J (2007) Evidence for Positive Selection in the C-terminal Domain of the Cholesterol Metabolism Gene PCSK9 Based on Phylogenetic Analysis in 14 Primate Species. PLoS ONE 2, e1098.
45. Li J, Tumanut C, Gavigan J A, Huang W J, Hampton E N, Tumanut R, Suen K F, Trauger J W, Spraggon G, Lesley S A, Liau G, Yowe D & Harris J L (2007) Secreted PCSK9 promotes LDL receptor degradation independently of proteolytic activity. Biochem J 406, 203-207.

46. McNutt M C, Lagace T A & Horton J D (2007) Catalytic activity is not required for secreted PCSK9 to reduce low density lipoprotein receptors in HepG2 cells. J Biol Chem 282, 20799-20803.
47. Fisher T S, Lo Surdo P, Pandit S, Mattu M, Santoro J C, Wisniewski D, Cummings R T, Calzetta A, Cubbon R M, Fischer P A, Tarachandani A, De Francesco R, Wright S D, Sparrow C P, Carfi A & Sitlani A (2007) PCSK9-dependent LDL receptor regulation: Effects of pH and LDL. J Biol. Chem.
48. Lopez D (2008) PCSK9: An enigmatic protease. Biochim Biophys Acta.
49. Elagoz A, Benjannet S, Mammarbassi A, Wickham L & Seidah N G (2002) Biosynthesis and cellular trafficking of the convertase SKI-1/SIP: ectodomain shedding requires SKI-1 activity. J Biol Chem 277, 11265-11275.
50. Chowdhury P S, Gallo M & Pastan I (2001) Generation of high titer antisera in rabbits by DNA immunization. J Immunol Methods 249, 147-154.

The embodiments of the invention in which an exclusive property or privilege is claimed are defined as follows:

1. A purified proprotein convertase subtilisin/kexin type 9 (PCSK9) polypeptide fragment consisting of the amino acid sequence VLALRSEEDGLAEAP (SEQ ID NO:2) or VLALRS(phos)EEDGLAEAP (SEQ ID NO:3), wherein (phos) indicates phosphorylation of the preceding amino acid.

2. The PCSK9 polypeptide fragment of claim 1, consisting of the amino acid sequence VLALRSEEDGLAEAP (SEQ ID NO:2).

3. The PCSK9 polypeptide fragment of claim 1, consisting of the amino acid sequence VLALRS(phos)EEDGLAEAP (SEQ ID NO:3).

4. A purified nucleotide sequence encoding the PCSK9 polypeptide fragment of claim 1.

5. A composition comprising the PCSK9 polypeptide fragment according to claim 1 and a pharmaceutically acceptable carrier, diluent or excipient.

6. A kit comprising,
a) the PCSK9 polypeptide fragment of claim 1;
b) a nucleic acid encoding the PCSK9 polypeptide fragment of claim 1;
c) a combination of (a) and (b); or
d) a composition comprising (a), (b), or (c) and one or more pharmaceutically acceptable carriers, diluents, or excipients;
and optionally further comprising one or both of:
e) one or more devices for delivering or administering said PCSK9 polypeptide fragment or said composition comprising said PCSK9 polypeptide fragment; and
f) instructions for administering said PCSK9 polypeptide fragment or said composition comprising said PCSK9 polypeptide fragment.

7. A vector comprising the nucleotide sequence of claim 4.

* * * * *

SEQUENCE LISTING

```
<160> NUMBER OF SEQ ID NOS: 5

<210> SEQ ID NO 1
<211> LENGTH: 692
<212> TYPE: PRT
<213> ORGANISM: homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285
```

```
Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                    325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
        450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 2
```

-continued

```
<211> LENGTH: 15
<212> TYPE: PRT
<213> ORGANISM: homo sapiens

<400> SEQUENCE: 2

Val Leu Ala Leu Arg Ser Glu Glu Asp Gly Leu Ala Glu Ala Pro
1               5                   10                  15

<210> SEQ ID NO 3
<211> LENGTH: 15
<212> TYPE: PRT
<213> ORGANISM: homo sapiens
<220> FEATURE:
<221> NAME/KEY: MOD_RES
<222> LOCATION: (6)..(6)
<223> OTHER INFORMATION: Phosphorylation of serine amino acid

<400> SEQUENCE: 3

Val Leu Ala Leu Arg Xaa Glu Glu Asp Gly Leu Ala Glu Ala Pro
1               5                   10                  15

<210> SEQ ID NO 4
<211> LENGTH: 13
<212> TYPE: PRT
<213> ORGANISM: homo sapiens

<400> SEQUENCE: 4

Arg Ser Arg His Leu Ala Gln Ala Ser Gln Glu Leu Gln
1               5                   10

<210> SEQ ID NO 5
<211> LENGTH: 13
<212> TYPE: PRT
<213> ORGANISM: homo sapiens
<220> FEATURE:
<221> NAME/KEY: MOD_RES
<222> LOCATION: (9)..(9)
<223> OTHER INFORMATION: Phosphorylation of serine amino acid

<400> SEQUENCE: 5

Arg Ser Arg His Leu Ala Gln Ala Xaa Gln Glu Leu Gln
1               5                   10
```